(12) United States Patent
Ishimaru et al.

(10) Patent No.: US 9,983,475 B2
(45) Date of Patent: May 29, 2018

(54) FLUORINATED SULFONATE ESTERS OF ARYL KETONES FOR NON-IONIC PHOTO-ACID GENERATORS

(71) Applicants: International Business Machines Corporation, Armonk, NY (US); Central Glass Co., Ltd., Yamaguchi (JP)

(72) Inventors: Takehisa Ishimaru, Tokyo (JP); Satoru Narizuka, Kawagoe (JP); Daniel P. Sanders, San Jose, CA (US); Ratnam Sooriyakumaran, San Jose, CA (US); Hoa D. Truong, San Jose, CA (US); Rudy J. Wojtecki, San Jose, CA (US)

(73) Assignees: International Business Machines Corporation, Armonk, NY (US); Central Glass Co., Ltd., Ube-shi, Yamaguchi (JP)

( * ) Notice: Subject to any disclaimer, the term of this patent is extended or adjusted under 35 U.S.C. 154(b) by 12 days.

(21) Appl. No.: 15/235,410

(22) Filed: Aug. 12, 2016

(65) Prior Publication Data
US 2018/0046077 A1 Feb. 15, 2018

(51) Int. Cl.
| | | |
|---|---|---|
| G03F 7/004 | (2006.01) |
| G03F 7/38 | (2006.01) |
| G03F 7/039 | (2006.01) |
| G03F 7/038 | (2006.01) |
| G03F 7/16 | (2006.01) |
| G03F 7/20 | (2006.01) |
| G03F 7/32 | (2006.01) |
| C07C 309/69 | (2006.01) |
| C07C 309/68 | (2006.01) |
| C07C 309/70 | (2006.01) |
| C07F 7/21 | (2006.01) |
| C07C 309/76 | (2006.01) |
| C07C 317/14 | (2006.01) |
| C07C 317/10 | (2006.01) |
| C07C 317/04 | (2006.01) |
| C07C 317/06 | (2006.01) |
| C07C 317/08 | (2006.01) |
| C07C 317/32 | (2006.01) |
| C07C 317/24 | (2006.01) |
| C07C 317/26 | (2006.01) |

(52) U.S. Cl.
CPC .......... *G03F 7/0045* (2013.01); *C07C 309/68* (2013.01); *C07C 309/69* (2013.01); *C07C 309/70* (2013.01); *C07C 309/76* (2013.01); *C07C 317/04* (2013.01); *C07C 317/06* (2013.01); *C07C 317/08* (2013.01); *C07C 317/10* (2013.01); *C07C 317/14* (2013.01); *C07C 317/24* (2013.01); *C07C 317/26* (2013.01); *C07C 317/32* (2013.01); *C07F 7/21* (2013.01); *G03F 7/0382* (2013.01); *G03F 7/0392* (2013.01); *G03F 7/168* (2013.01); *G03F 7/2004* (2013.01); *G03F 7/322* (2013.01); *G03F 7/38* (2013.01); *C07C 2103/74* (2013.01)

(58) Field of Classification Search
CPC ........ G03F 7/0045; G03F 7/0397; G03F 7/38; C07C 317/04; C07C 317/06; C07C 317/08; C07C 317/10; C07C 317/14; C07C 317/24; C07C 317/26; C07C 317/32
USPC ....... 430/270.1, 919, 921, 326, 330; 568/28, 568/30, 31, 32, 33, 34, 35
See application file for complete search history.

(56) References Cited

U.S. PATENT DOCUMENTS

| | | | |
|---|---|---|---|
| 2,322,760 A | 6/1943 | Lantz | |
| 5,135,838 A | 8/1992 | Houlihan et al. | |
| 5,304,456 A | 4/1994 | Ueda et al. | |
| 5,830,619 A | 11/1998 | Chin et al. | |
| 6,855,476 B2 * | 2/2005 | Ferreira | C07C 309/10 430/270.1 |
| 7,960,087 B2 | 6/2011 | Kodama | |
| 8,158,330 B2 | 4/2012 | Harada et al. | |
| 8,163,461 B2 | 4/2012 | Ober et al. | |
| 8,329,377 B2 | 12/2012 | Takemoto et al. | |
| 9,223,208 B2 * | 12/2015 | Tsuchimura | C07C 317/44 |

(Continued)

FOREIGN PATENT DOCUMENTS

| | | |
|---|---|---|
| EP | 0717319 B1 | 11/2001 |
| JP | 2002236358 A | 8/2002 |

(Continued)

OTHER PUBLICATIONS

Hinsberg, et al., "Effect of Resist Components on Image Spreading During Postexposure Bake of Chemically Amplified Resists", Proceedings of SPIE vol. 3999 (2000), pp. 148-160.
McGeary, et al., "An 'inside-out' approach to suramin analogues", Tetrahedron 65 (2009), 3990-3997.
Storer, et al., "Aracyl triflates for preparing fluorescent and UV absorbing derivatives of unreactive carboxylates, amines and other metabolites", Analytica Chimica Acta, vol. 558, Issues 1-2, Feb. 3, 2006, pp. 319-325.
U.S. Appl. No. 15/235,342, filed Aug. 12, 2016.
U.S. Appl. No. 15/235,673, filed Aug. 12, 2016.

*Primary Examiner* — John S Chu
(74) *Attorney, Agent, or Firm* — Michael R. Roberts

(57) ABSTRACT

Non-ionic photo-acid generating (PAG) compounds were prepared that contain an aryl ketone group having a perfluorinated substituent alpha to the ketone carbonyl. The non-polymeric PAGs release a sulfonic acid when exposed to high energy radiation such as deep UV or extreme UV light. The photo-generated sulfonic acid has a low diffusion rate in an exposed resist layer subjected to a post-exposure bake (PEB) at 100° C. to 150° C., resulting in formation of good line patterns after development. At higher temperatures, the PAGs can also undergo a thermal reaction to form a sulfonic acid. The perfluorinated substituent provides improved thermal stability and hydrolytic/nucleophilic stability.

24 Claims, 14 Drawing Sheets

(56) References Cited

U.S. PATENT DOCUMENTS

| | | | |
|---|---|---|---|
| 9,223,209 B2 | 12/2015 | Sanders et al. | |
| 9,244,345 B1 | 1/2016 | Ishimaru et al. | |
| 9,274,420 B2* | 3/2016 | Akiba | G03F 7/0045 |
| 2002/0197558 A1 | 12/2002 | Ferreira et al. | |
| 2012/0289738 A1 | 11/2012 | Hosoi et al. | |
| 2013/0122427 A1 | 5/2013 | Kataoka et al. | |
| 2014/0065541 A1* | 3/2014 | Akiba | G03F 7/0045 |
| | | | 430/283.1 |
| 2014/0087310 A1 | 3/2014 | Kato et al. | |
| 2014/0093823 A1* | 4/2014 | Brainard | G03F 7/0045 |
| | | | 430/283.1 |
| 2014/0193752 A1* | 7/2014 | Brainard | C07C 309/65 |
| | | | 430/283.1 |

FOREIGN PATENT DOCUMENTS

| | | | |
|---|---|---|---|
| JP | 2004519520 A | 7/2004 | |
| JP | 4145017 B2 | 9/2008 | |
| WO | 02082185 A1 | 10/2002 | |

* cited by examiner

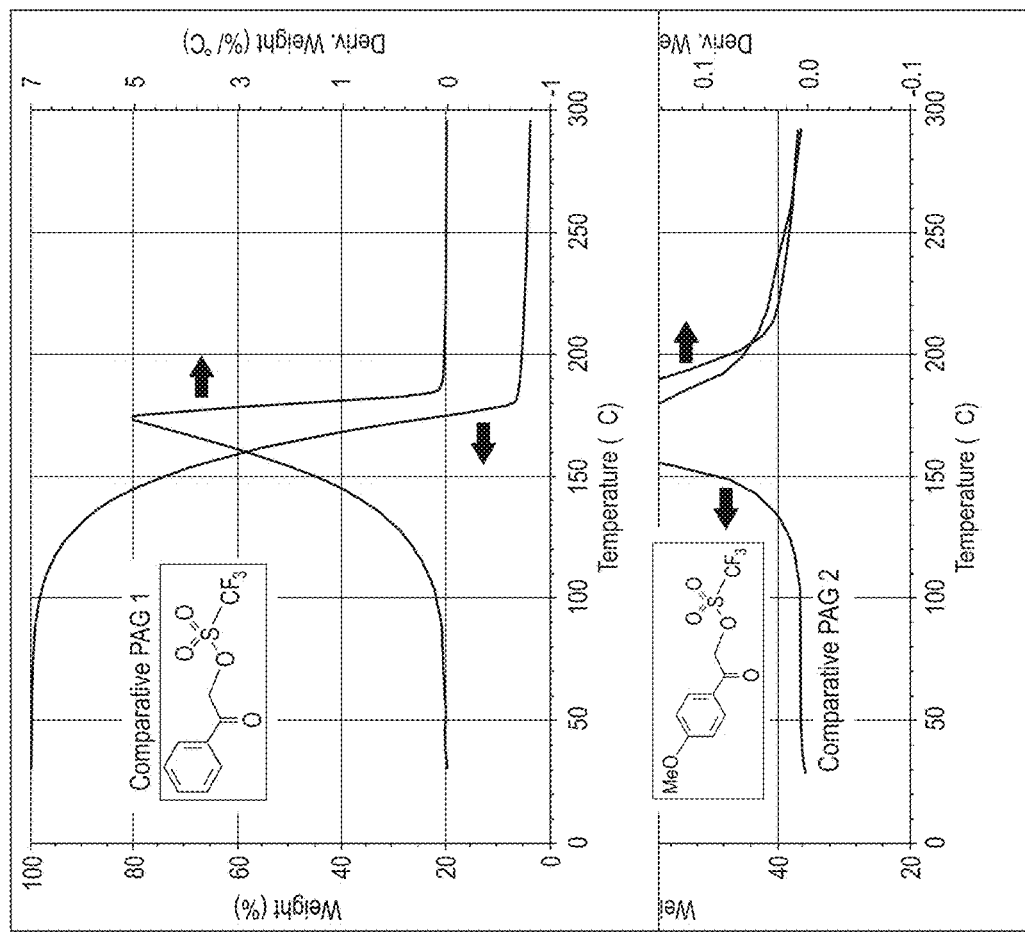

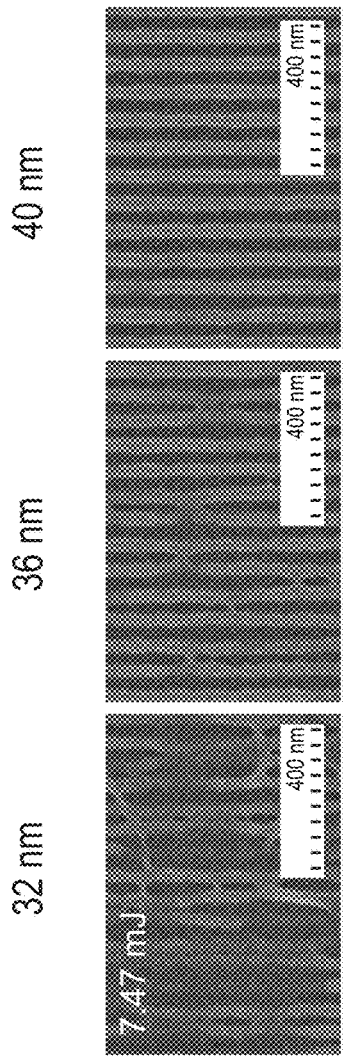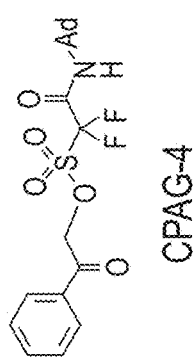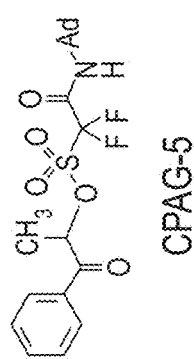
FIG. 9

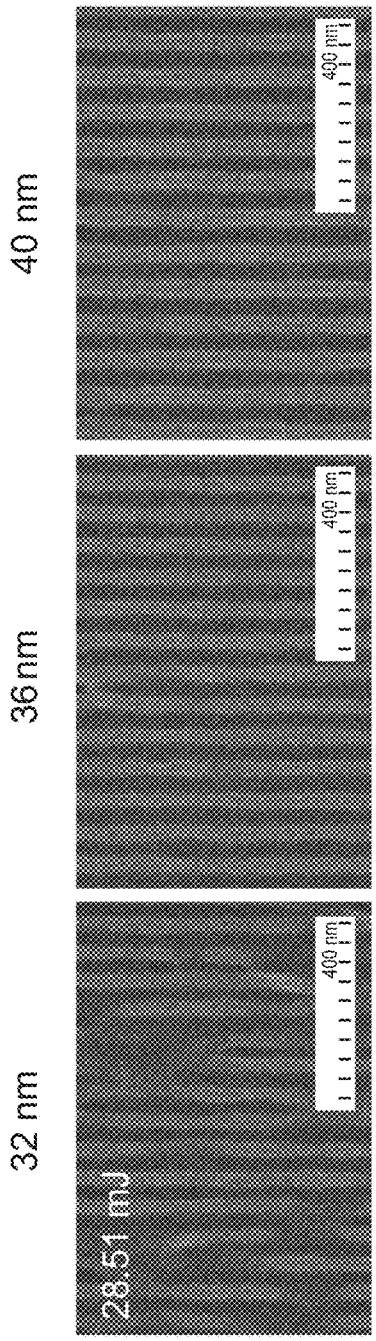
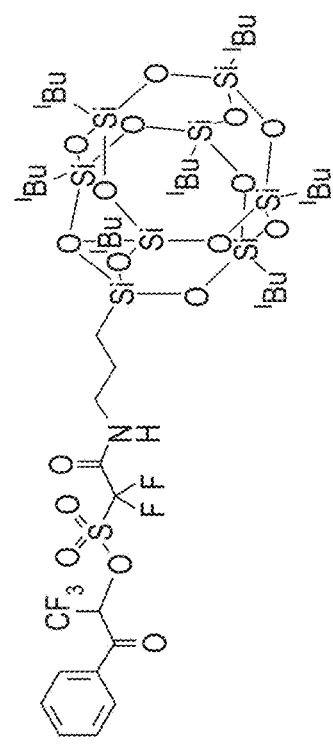
FIG. 11

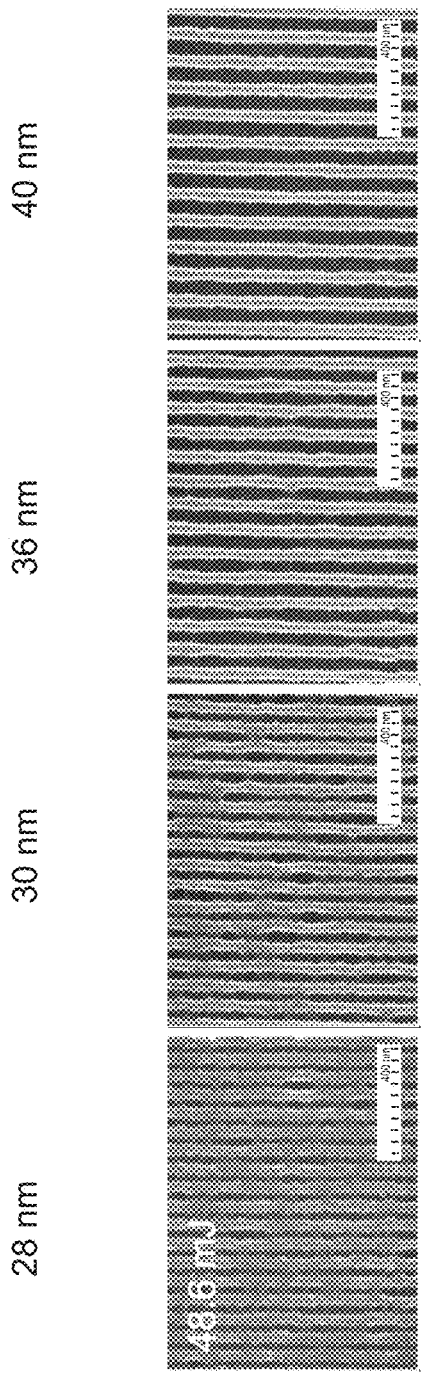
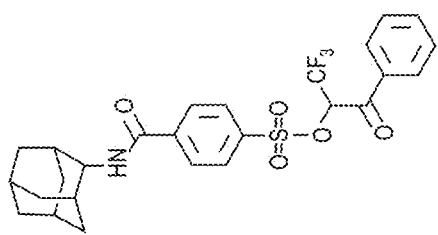
FIG. 12

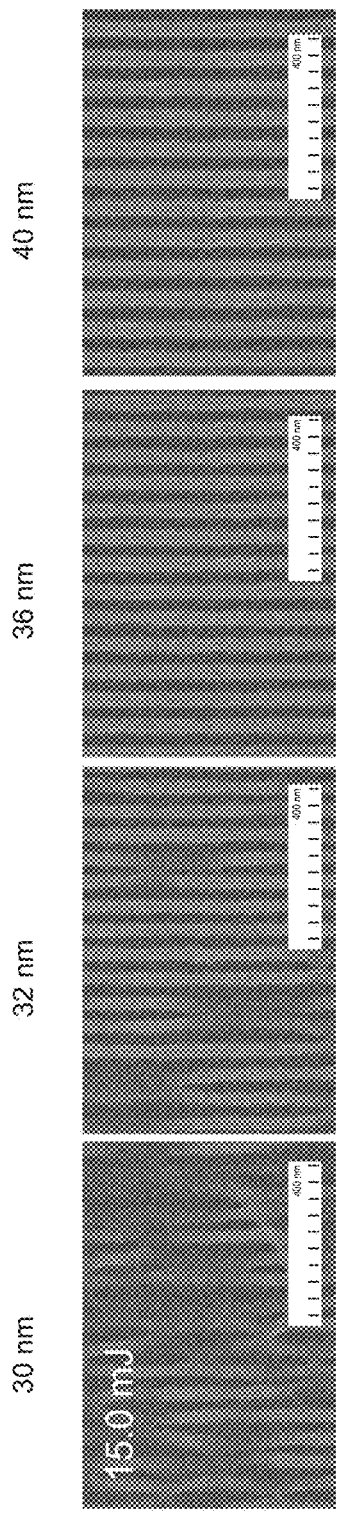
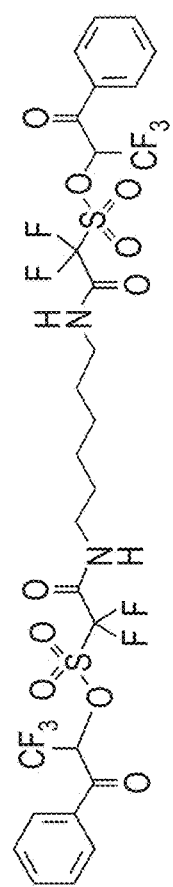
FIG. 13

FLUORINATED SULFONATE ESTERS OF ARYL KETONES FOR NON-IONIC PHOTO-ACID GENERATORS

BACKGROUND

The present invention relates to non-ionic low diffusing photo-acid generators (PAGs) for lithographic applications, and more specifically to PAGs comprising sulfonate esters of fluoroalkyl substituted alpha-hydroxy aryl ketones.

Extreme Ultraviolet (EUV) lithography is expected to succeed current 193 nm immersion lithography combined with multiple patterning enhancements as the next generation printing technique. EUV radiation, with a shorter wavelength of 13.5 nm, is expected to achieve sub-20 nm features in a single exposure process. However, more advances in efficient light sources, EUV masks, and resists are needed for EUV lithography to become a manufacturing process.

During the last few years, considerable effort has gone into the development of resists for EUV applications. However, the majority of the EUV resists have been modified from the resists developed for 193 nm and 248 nm applications.

The highest performing photoresists for 193 nm and 248 nm applications are all based on a chemical amplification mechanism. Chemically amplified photoresists utilize a catalytic mechanism to generate a relatively large number of chemical events (e.g., deprotection reactions in the case of positive tone photoresists, or crosslinking reactions in the case of negative tone photoresists). Application of a relatively low dose of radiation induces formation of the catalyst, often a strong acid, which then catalyzes the chemical events. The current positive resist compositions comprise aqueous base soluble functional groups that are sufficiently protected with acid-labile groups so that the resist initially will not dissolve in an aqueous base developer. During exposure to radiation, the photo-acid generator (PAG) present in the resist composition produces a strong acid, which then catalyzes the removal of the acid-labile groups upon heating exposed resist layer in a post-exposure bake (PEB). This process produces aqueous base soluble material in the exposed area, which then is selectively removed with a basic aqueous developer to produce the images.

One phenomenon that limits the resolution potential of the resists developed for 248 nm, 193 nm and E-beam applications is referred to as "image blur" (see, e.g., Hinsberg et al., Proc. SPIE, (2000), 3999, 148). Image blur is generally thought to result from two contributing factors: gradient-driven acid diffusion and reaction propagation, the result being a distortion in the developable image compared to the projected aerial image transferred onto the film. This becomes critical in EUV applications because of the need for small features with low line edge roughness (LER). Therefore, a need exists to control the gradient driven acid-diffusion in the resist films.

Most widely reported PAGs in the resist formulations are ionic in nature (triphenylsulfonium or iodonium sulfonates). Non-ionic PAGs have some advantages such as higher solubility in casting solvents and homogeneous distribution in the resist film. Previously, a few non-ionic PAGs having imide photo-labile groups have been reported (U.S. Pat. No. 8,329,377 B2 to Takemoto, et al.).

In the area of photo acid generators (PAGs), a limited number of PAGs having aryl ketone protecting groups have been reported. U.S. Pat. No. 5,304,456 to Ueda, et al., discloses PAGs with perfluoro alkyl sulfonic acids. WO02/082185/A1 (JP2004519520A) to Ferreira, et al., and JP2002236358A (JP4145017B2) to Kunihiko disclose PAGs with perfluoroalkyl and perfluoro ether substituted sulfonic acids. Similarly, aryl ketone triflate PAGs have been described by Storer, et al., Analytica Chimica Acta (2006), volume 558(1-2), pages 319-325. These previously reported aryl ketone PAGs produce volatile and highly diffusing sulfonic acids that can be unstable in resist formulations.

Therefore, a need exists for aryl ketone protected PAGs that have higher thermal and hydrolytic stability in resist formulations and produce less volatile, low diffusing sulfonic acids.

SUMMARY

Accordingly, a compound is disclosed of formula (3):

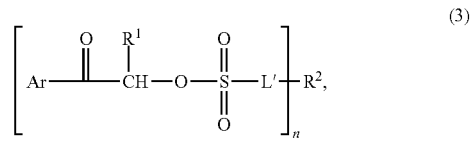

wherein
n is a positive integer having a value of 1-4,
Ar is a monovalent aryl radical comprising one or more aromatic rings,
L' is a single bond or a divalent $C_1$-$C_{10}$ linking group,
$R^1$ is a monovalent perfluorinated $C_1$-$C_{10}$ radical, wherein $R^1$ has a molecular formula consisting of elements carbon and fluorine, and
$R^2$ is a $C_1$-$C_{50}$ radical having a valency of n.

Also disclosed is a resist formulation, comprising:
a solvent;
a resin capable of chemical amplification;
a base quencher; and
an above-described PAG compound;
wherein
the resin, the base quencher, and the PAG compound are in contact with the solvent, and the resist formulation is suitable for use in a lithographic process.

Further disclosed is a method, comprising:
casting a resist formulation comprising a solvent, a resin capable of chemical amplification, a base, and an above-described compound on a surface of a substrate and removing the solvent, thereby forming a layered structure, the layered structure comprising a resist layer disposed on the surface of the substrate, the resist layer comprising the resin, the base quencher, and the compound;
optionally baking the resist layer;
exposing the resist layer pattern-wise to radiation, thereby forming an exposed resist layer comprising exposed regions of the resist layer and non-exposed regions of the resist layer, the exposed regions of resist layer comprising an acid formed by exposing the compound to the radiation;
heating the exposed resist layer, thereby forming a heated exposed resist layer comprising heated exposed regions and heated non-exposed regions; and
selectively removing the heated exposed regions or the heated non-exposed regions, thereby forming a patterned resist layer disposed on the surface of the substrate.

The above-described and other features and advantages of the present invention will be appreciated and understood by those skilled in the art from the following detailed description, drawings, and appended claims.

BRIEF DESCRIPTION OF THE SEVERAL VIEWS OF THE DRAWINGS

FIG. 4 is a graph showing the thermogravimetric analysis (TGA) curves for CPAG-1 (comparative Example 18).

FIG. 5 is a graph showing the TGA curves for CPAG-2 (comparative Example 19).

FIG. 9 is a set of scanning electron micrograph (SEM) images comparing line patterns formed with CPAG-4 and CPAG-5 when exposed at 13.5 nm using the extreme ultraviolet micro exposure tool (EUV-MET).

FIG. 11 is a set of SEM images showing line patterns formed with PAG-4 when exposed at 13.5 nm using the EUV-MET.

FIG. 12 is a set of SEM images showing line patterns formed with PAG-6 when exposed at 13.5 nm using the EUV-MET.

FIG. 13 is a set of SEM images showing line patterns formed with DPAG-1 when exposed at 13.5 nm using the EUV-MET.

DETAILED DESCRIPTION

Figure 1A:
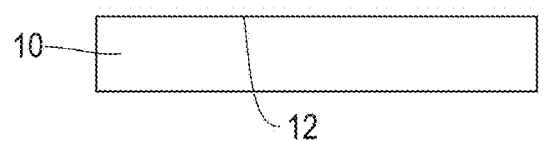
FIGS. 1A to 1E are schematic layer diagrams showing a method of forming a multi-layered structure that includes a topographical patterned layer comprising exposed resist composition.

Photo-acid generating (PAG) compounds are disclosed that comprise an aryl ketone group having a perfluorinated alkyl substituent alpha to the ketone carbonyl. The PAGs show improved diffusion, thermal stability, and hydrolytic stability properties for lithographic applications compared to otherwise identical compounds in which the perfluorinated alkyl substituent is replaced with a corresponding non-fluorinated hydrocarbon group or hydrogen. A lithographic exposure of a resist layer containing the disclosed non-polymeric PAGs releases a sulfonic acid. The released acid can have a low diffusion rate when the exposed resist layer is heated in a post-exposure bake (PEB) at a temperature in a range of about 100° C. to 150° C. Also disclosed are resist compositions comprising the non-ionic PAG compounds and lithographic methods of forming resist patterns therefrom. Hereinafter, it should be understood that the PAGs are non-ionic prior to a lithographic exposure unless otherwise stated.

The PAGs are capable of forming an acid when exposed to radiation having a wavelength between 0 nm and 300 nm, including electron beam (E-beam) radiation, extreme ultraviolet radiation (EUV) having a wavelength of about 4-124 nm, soft x-ray, x-ray, γ-ray, and/or deep ultraviolet radiation (DUV) having a wavelength of about 125-250 nm (e.g., ArF excimer laser at 193 nm and KrF excimer laser at 248 nm). The PAGs can be relatively insensitive to DUV compared to EUV. As a result, EUV exposures of resists layers comprising the PAGs can produce lithographic patterns having fewer defects associated with out of band (OOB) radiation. In an embodiment, the lithographic process utilizes an ultraviolet wavelength of 13.5 nm (EUV) to expose a resist film comprising a disclosed PAG compound.

The PAG compounds are generally thermally stable up to at least 130° C. by thermogravimetric analysis (TGA). In an embodiment, the PAG compounds are thermally stable up to at least 140° C. by TGA.

The PAG compounds can be used singularly or in combination to form a resist composition. A resist composition can comprise a PAG compound as the sole photo-acid generating material.

The term "positive-tone development" means the exposed areas of the resist layer are selectively removed during development by a given developer. The exposed areas can become more soluble in a given developer (e.g., aqueous alkaline developer) by, for example, a non-crosslinking chemical reaction induced by the exposure that increases the polarity of the exposed areas, thereby increasing solubility of the exposed areas relative to non-exposed areas in a given polar developer.

The term "negative-tone development" means the non-exposed areas of the resist layer are selectively removed during development. In this instance, the exposed areas of the resist layer can become less soluble in a given developer compared to the non-exposed areas. For example, a cross-linking reaction or some other chemical change induced by the exposure can lower the solubility of the exposed areas relative to non-exposed areas in a given developer.

The term "positive-tone resist pattern" refers to the resist layer containing non-exposed resist that remains after positive-tone development. The examples further below illustrate formation of positive-tone resist patterns using the PAG compounds.

The term "negative-tone resist pattern" refers to the resist layer containing exposed resist that remains after negative tone development.

The PAG compounds can be used to form a positive-tone resist pattern or a negative tone resist pattern.

PAG Compounds

The PAG compounds comprise an aryl ketone group having a structure according to formula (1):

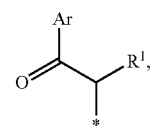

(1)

wherein

Ar is a monovalent radical comprising one or more aromatic rings, and $R^1$ is a monovalent perfluorinated $C_1$-$C_{10}$ radical, wherein $R^1$ has a molecular formula consisting of elements carbon and fluorine.

Herein, a bond to an asterisk indicates the atomic center linked to the asterisk is covalently linked to another unspecified atomic center of the chemical structure. The asterisk represents the unspecified atomic center. In this instance, a methylene carbon is shown linked to an asterisk. The asterisk represents an oxygen of a sulfonate ester, as shown further below.

Herein, a perfluorinated group is a non-charged functional group whose molecular formula contains only the elements carbon and fluorine. The perfluorinated group contains no hydrogen or heteroatoms (oxygen, nitrogen, sulfur, and so on). A given pair of adjacent carbons of the perfluorinated group can be linked by a single bond, double bond, or triple bond. Preferably, adjacent carbons are linked by a single bond (i.e., $R^1$ is a perfluorinated alkyl group, meaning an alkyl group in which each hydrogen is replaced by fluorine). Exemplary $R^1$ groups include trifluoromethyl (*—$CF_3$), perfluoroethyl (*—$CF_2CF_3$), perfluoro-n-propyl (*—$CF_2CF_2CF_3$), perfluoroisopropyl (*—$CF(CF_3)_2$), perfluoro-n-butyl (*—$CF_2CF_2CF_2CF_3$), perfluoroisobutyl (*—$CF_2CF(CF_3)_2$), perfluoro-n-pentyl (*—$CF_2(CF_2)_3CF_3$), and pentafluorophenyl. In an embodiment, $R^1$ is selected from the group consisting of trifluoromethyl, and trifluoroethyl.

More specific aryl ketone groups have a structure according to formula (2):

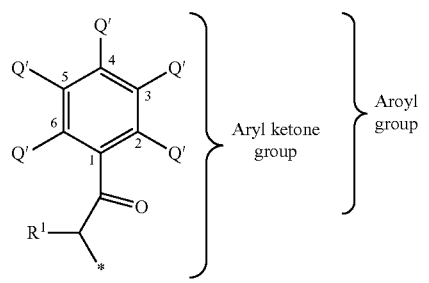

(2)

wherein
carbons of the aromatic ring are numbered 1-6,
each Q' is selected from the group consisting of hydrogen, halides, alkyl groups, fluoroalkyl groups, cycloalkyl groups, alkoxy groups, substituted and unsubstituted aryl groups, and substituted and unsubstituted aryloxy groups,
$R^1$ is a monovalent perfluorinated $C_1$-$C_{10}$ radical, wherein $R^1$ has a molecular formula consisting of elements carbon and fluorine, and
optionally, adjacent Q' groups complete a ring.

Exemplary non-limiting Q' groups include methyl, ethyl, isopropyl, t-butyl, hexyl, cyclohexyl, norbornyl, trifluoromethyl, trifluoroethyl, methoxy, ethoxy, propyloxy, butoxy, t-butoxy, phenyl, ortho-fluorophenyl, meta-fluorophenyl, para-fluorophenyl, pentafluorophenyl, and naphthyl.

Exemplary non-limiting aryl groups Ar include those of Scheme 1.

Scheme 1

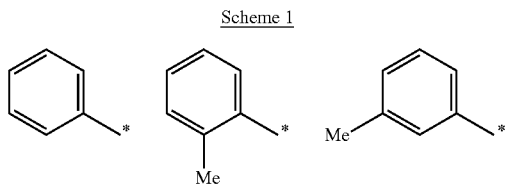

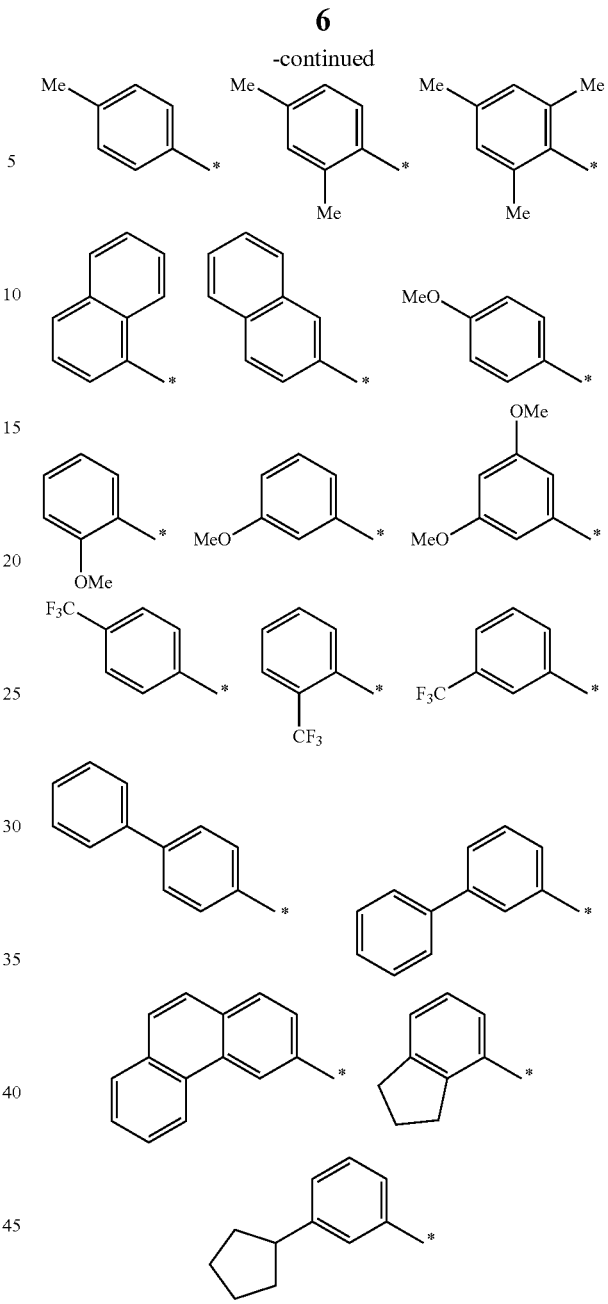

Exemplary non-limiting aroyl groups include those of Scheme 2.

Scheme 2

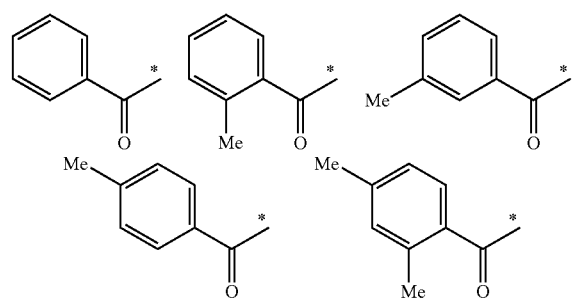

-continued
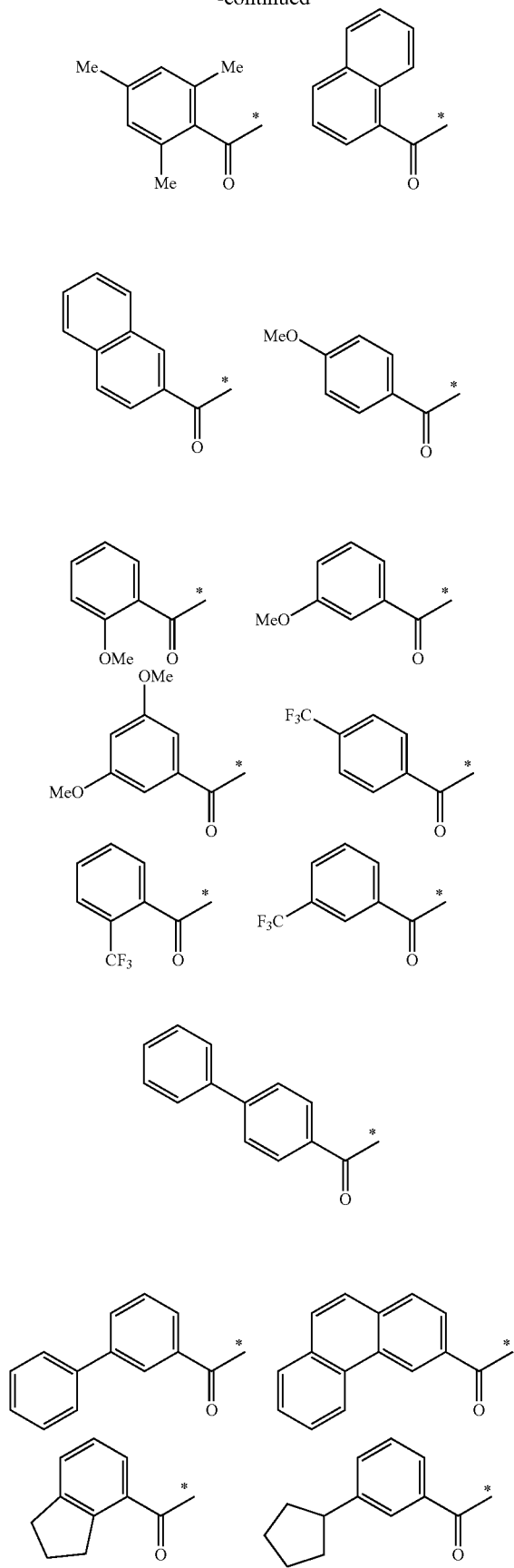
Exemplary non-limiting aryl ketone groups include those of Scheme 3.
Scheme 3
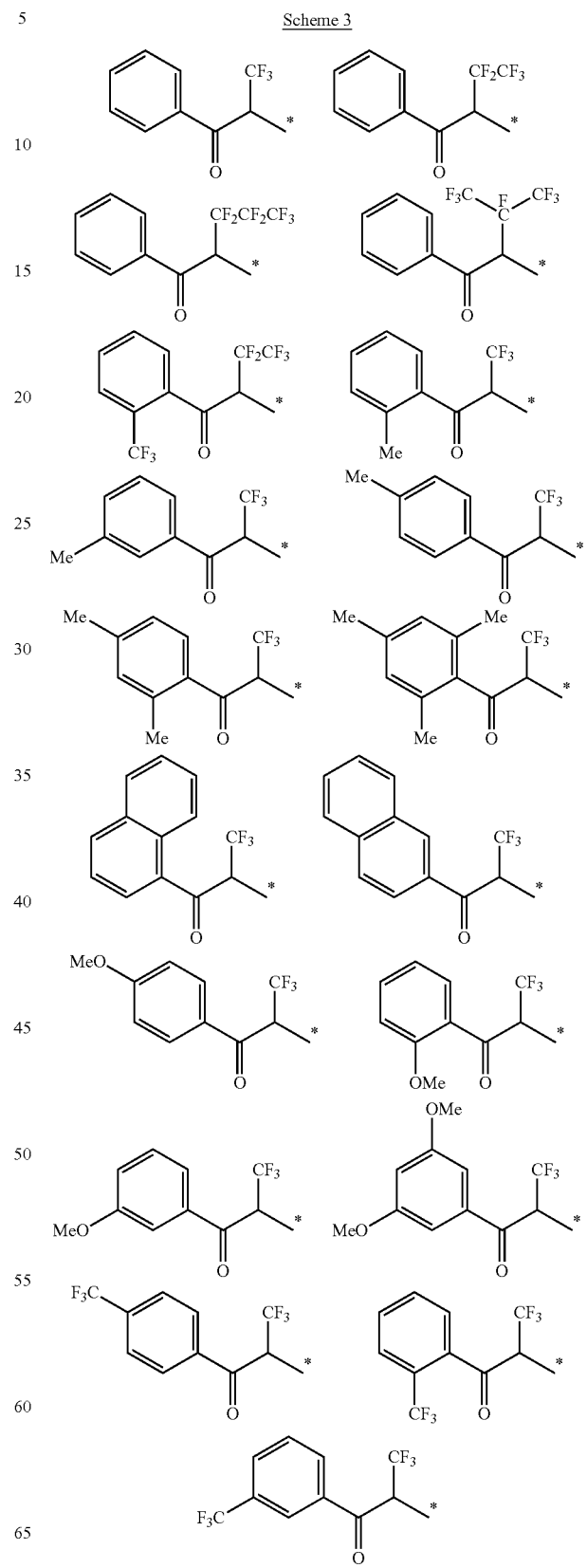

-continued

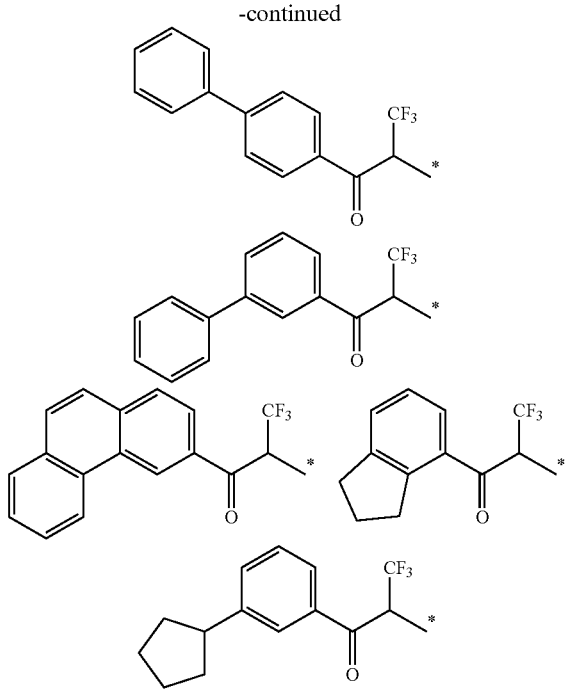

The PAG has a structure according to formula (3):

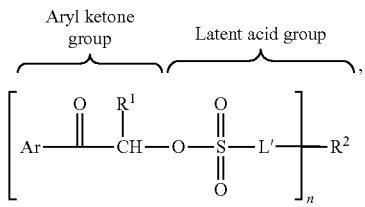

wherein
n is a positive integer having a value of 1 to 4,
Ar is a monovalent aryl radical comprising one or more aromatic rings,
L' is a single bond or a divalent $C_1$-$C_{10}$ linking group,
$R^1$ is a monovalent perfluorinated $C_1$-$C_{10}$ radical, wherein $R^1$ has a molecular formula consisting of elements carbon and fluorine, and
$R^2$ is a $C_1$-$C_{50}$ radical having a valency of n.
In an embodiment, n is 1 or 2.
No particular restriction is placed on the $C_1$-$C_{10}$ linking groups (L'). These L' groups can be any suitable linking group, with the proviso that the desirable properties of photogeneration, thermal stability and low diffusion are not adversely affected. For example, the L' groups can comprise an alkylene, phenylene, ester, amide, carbamate, urea, and/or ether functional group, which joins the sulfonate sulfur to $R^1$. Non-limiting exemplary L' groups include the following:

i)

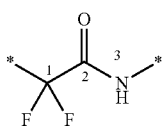

wherein amide nitrogen 3 is linked to $R^1$, ii)

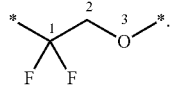

wherein ether oxygen 3 is linked to $R^1$, iii)

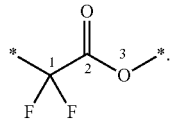

wherein ester oxygen 3 is linked to $R^1$, iv)

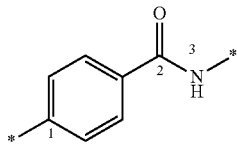 [SMILES: *NC(=O)c1ccc(*)cc1]

wherein amide nitrogen 3 is linked to $R^1$, and wherein carbon 1 of each of the foregoing groups is linked to the sulfonate sulfur of formula (3).

The $R^2$ groups are described in more detail further below.

More specific PAG compounds have a structure according to formula (4):

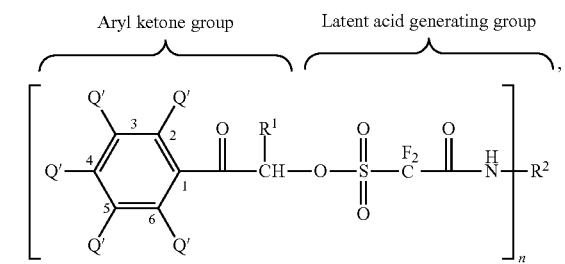

wherein
aromatic carbons of the aryl ketone group are numbered 1-6,
n is a positive integer having a value of 1 to 4,
each Q' is selected from the group consisting of hydrogen, halides, alkyl groups, fluoroalkyl groups, cycloalkyl groups, alkoxy groups, substituted and unsubstituted aryl groups, substituted and unsubstituted aryloxy groups, and a covalent bond which is linked to and completes a ring with an adjacent foregoing Q' group,
$R^1$ is a monovalent perfluorinated $C_1$-$C_{10}$ radical, wherein $R^1$ has a molecular formula consisting of elements carbon and fluorine, and
$R^2$ is a $C_1$-$C_{50}$ radical having a valency of n.
$R^2$ is a non-polymerizable group. Otherwise, no particular restriction is placed on the structure of $R^2$, with the proviso that R² does not adversely affect the desirable acid generation, diffusion, and thermal properties of the PAG compound. Preferably, R² comprises 6-50 carbons.

Monovalent R² Groups (n=1)

Exemplary non-limiting monovalent R² groups include branched and unbranched alkyl groups (e.g., methyl, ethyl, n-propyl, isopropyl, n-butyl, isobutyl, t-butyl, n-pentyl, isopentyl, neopentyl, n-hexyl ($C_6H_{13}$), 3,3-dimethylbutan-2-yl, n-heptyl ($C_7H_{15}$), n-octyl ($C_8H_{17}$), octan-2-yl, 6-methylheptan-2-yl, n-nonyl ($C_9H_{19}$), nonan-2-yl, n-decyl ($C_{10}H_{21}$), n-undecyl ($C_{11}H_{23}$), n-dodecyl ($C_{12}H_{25}$), n-tridecyl ($C_{13}H_{27}$), n-tetradecyl ($C_{14}H_{29}$), n-pentadecyl ($C_{15}H_{31}$), n-hexadecyl ($C_{16}H_{33}$), n-heptadecyl ($C_{17}H_{35}$), n-octadecyl ($C_{18}H_{37}$), n-nonadecyl ($C_{19}H_{39}$), and n-icosyl ($C_{20}H_{41}$).

Other monovalent R² groups include substituted and unsubstituted, branched and unbranched, $C_6$-$C_{20}$ monocyclo-, bicyclo-, and tricyclo-alkanes such as those of Scheme 4.

Scheme 4

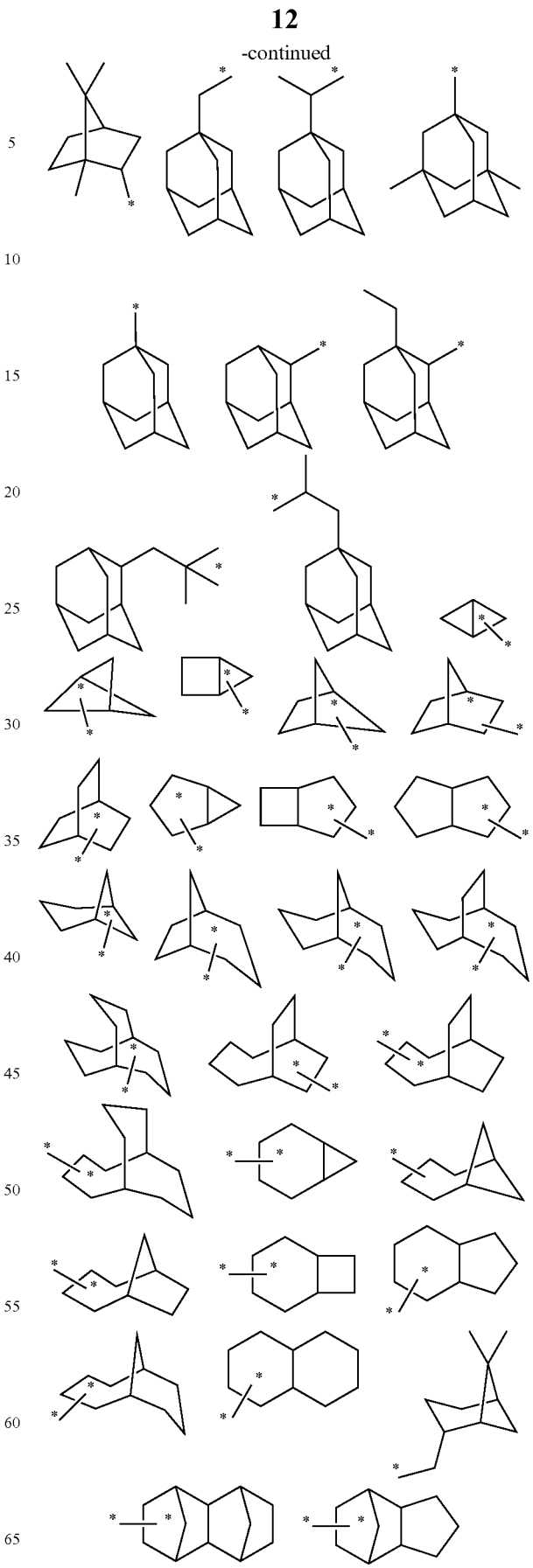

A bond with two asterisks crossing a bond means one end of the bond can be linked to any one of the carbons of the structure, and the other end of the bond is linked to the nitrogen of formula (4). As an example, the structure

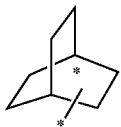

includes the following structures,

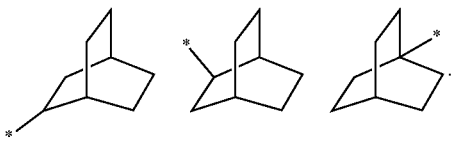

Other non-limiting monovalent $R^2$ groups include substituted and unsubstituted aromatic groups, such as those of Scheme 5.

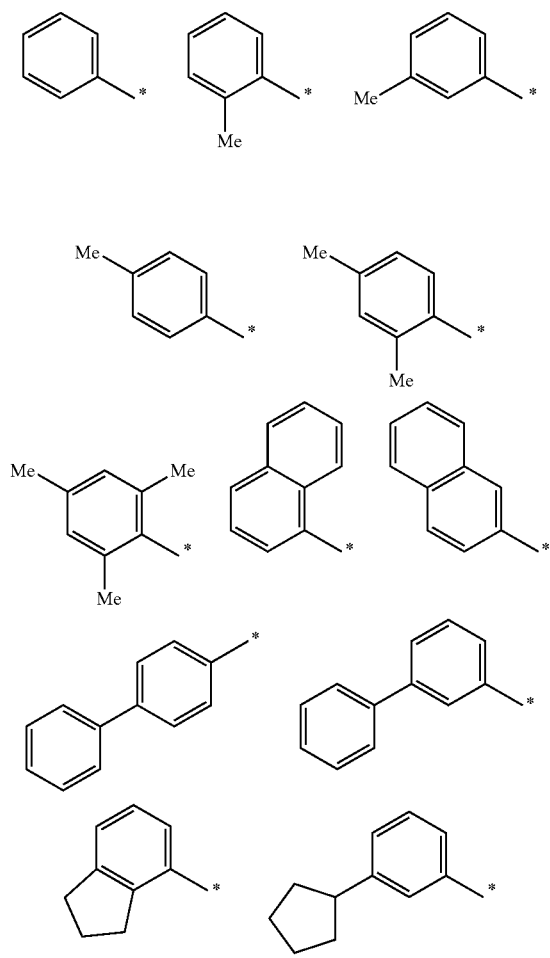

Scheme 5

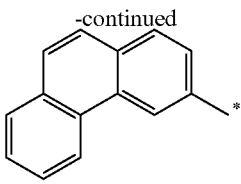

Still other monovalent $R^2$ groups comprise a silsesquioxane group and have a structure of formula (5):

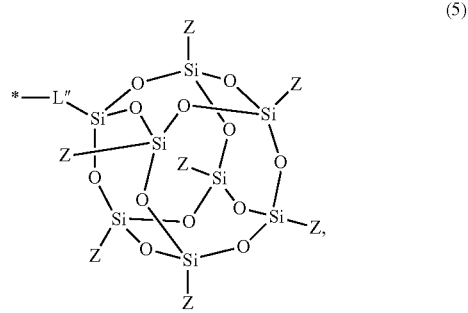

(5)

wherein
L" is a divalent $C_1$-$C_6$ linking group, and
Z is a $C_1$-$C_6$ alkyl group.

Non-limiting exemplary Z groups include methyl, ethyl, propyl, isopropyl, n-butyl, isobutyl, n-pentyl, isopentyl, and n-hexyl.

Non-limiting exemplary L" groups include divalent hydrocarbylene groups (e.g., methylene (*—CH$_2$—*), ethan-1,2-diyl (*—CH$_2$CH$_2$—*), propan-1,3-diyl (*—CH$_2$CH$_2$CH$_2$—*), propan-1,2-diyl (*—CH(CH$_3$)CH$_2$—*), butan-1,4-diyl (*—CH$_2$(CH$_2$)$_2$CH$_2$—*), pentan-1,5-diyl (*—CH$_2$(CH$_2$)$_3$CH$_2$—*), hexan-1,6-diyl (*—CH$_2$(CH$_2$)$_4$CH$_2$—*)), 1,3-phenylene, and 1,4-phenylene. In an embodiment, $R^2$ is

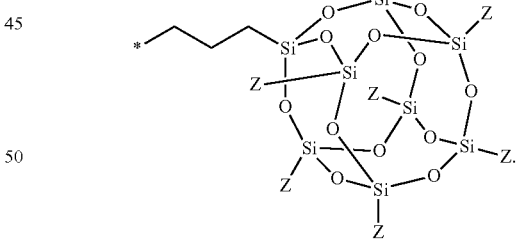

Z = isobutyl

Divalent $R^2$ Groups (n=2)

Exemplary non-limiting divalent $R^2$ groups include branched and unbranched divalent hydrocarbylene groups (e.g., ethan-1,2-diyl (*—CH$_2$CH$_2$—*), propan-1,3-diyl (*—CH$_2$CH$_2$CH$_2$—*), propan-1,2-diyl (*—CH(CH$_3$)CH$_2$—*), butan-1,4-diyl (*—CH$_2$(CH$_2$)$_2$CH$_2$—*), butan-1,3-diyl (*—CH$_2$CH$_2$CH(CH$_3$)—*), pentan-1,5-diyl (*—CH$_2$(CH$_2$)$_3$CH$_2$—*), and hexan-1,6-diyl (*—CH$_2$(CH$_2$)$_4$CH$_2$—*), heptan-1,7-diyl (*—CH$_2$(CH$_2$)$_5$CH$_2$—*), octan-1,8-diyl (*—CH$_2$(CH$_2$)$_6$CH$_2$—*), and nonan-1,9-diyl (*—CH$_2$(CH$_2$)$_7$CH$_2$—*)).

Other non-limiting divalent R² groups include those of Scheme 6.

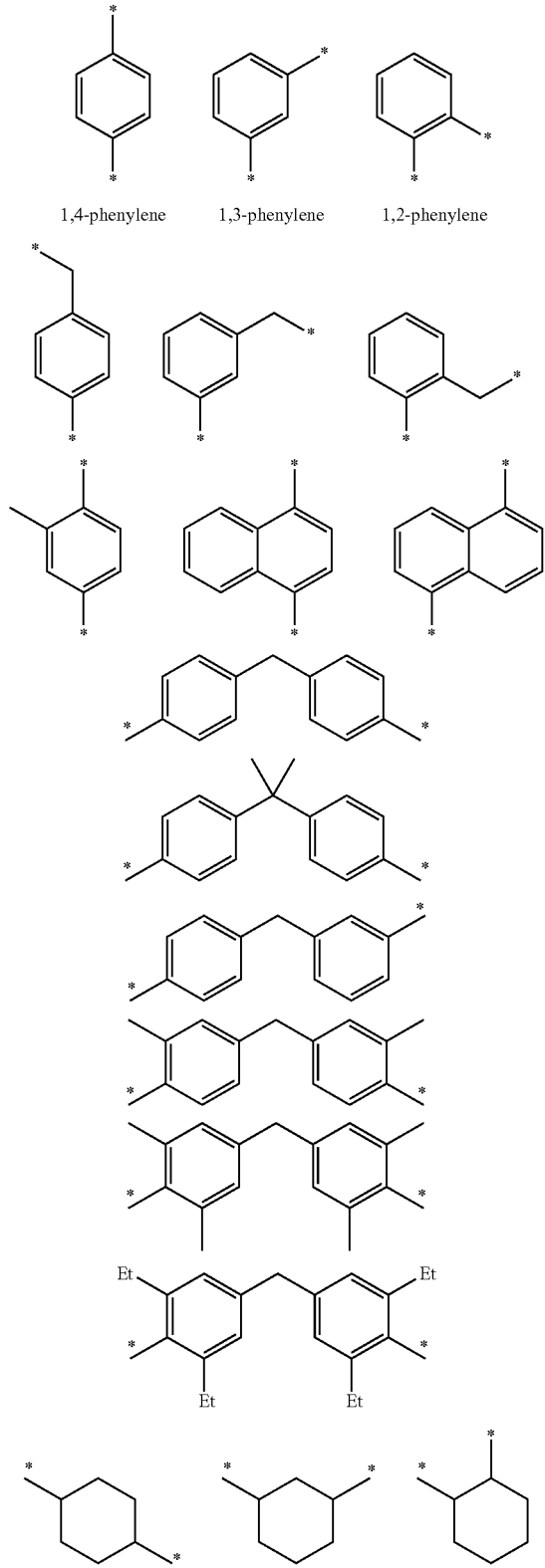

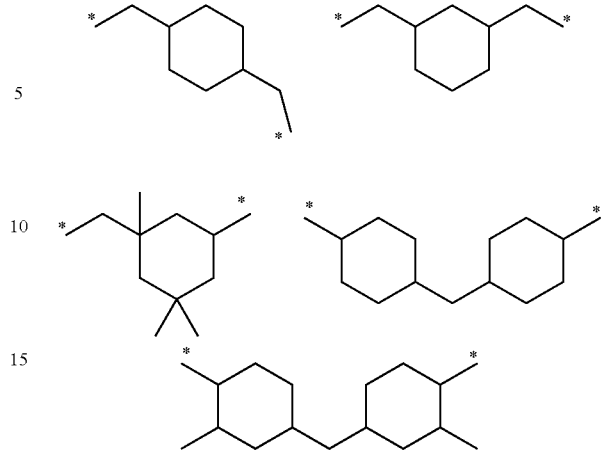

In an embodiment, R² is 1,6-hexylene (*—CH$_2$(CH$_2$)$_4$CH$_2$—*).

The aryl ketone groups and/or R² groups can be stereospecific or non-stereospecific.

Trivalent R² Groups (n=3)

Exemplary non-limiting trivalent R² groups include branched and unbranched, cyclic and acyclic trivalent hydrocarbon groups having 3 to 2, such as those of Scheme 7.

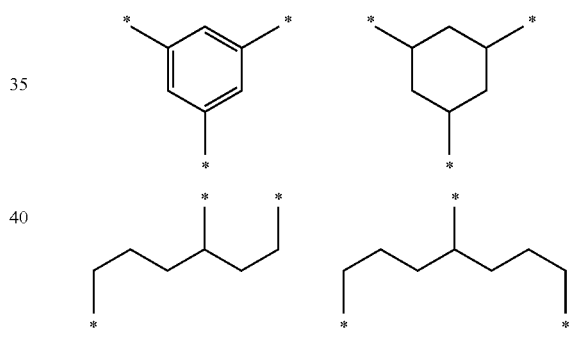

Tetravalent R² groups (n = 4)

Exemplary non-limiting tetravalent R² groups include branched and unbranched, cyclic and acyclic tetravalent hydrocarbon groups having 3-20 carbons, such as those of Scheme 8.

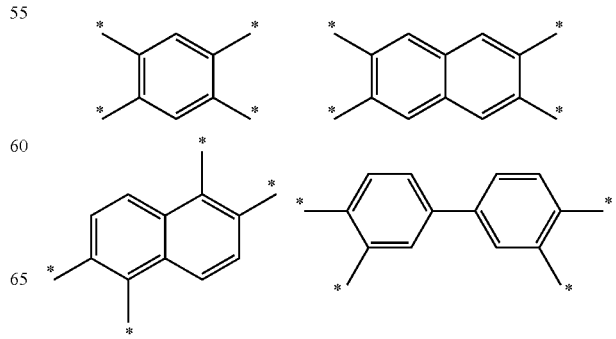

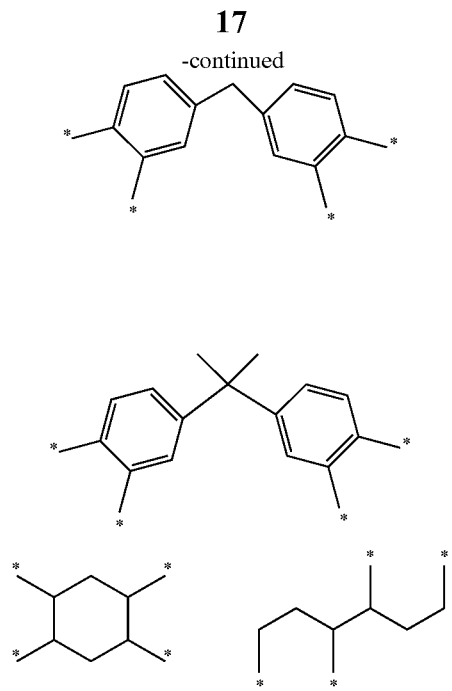

Exemplary non-limiting PAG compounds include those of Scheme 9. The tricyclic structure in PAG-1 and PAG-6 is adamantan-1-yl.

Scheme 9

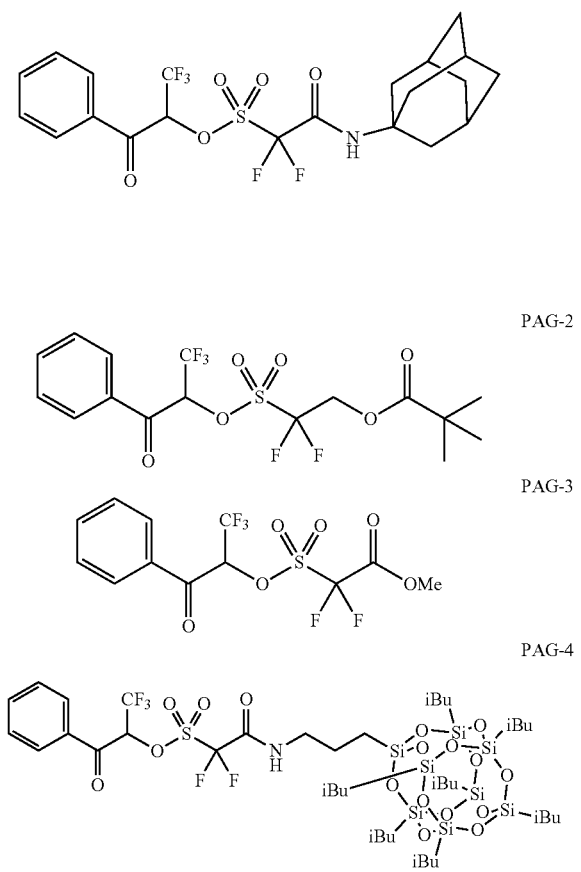

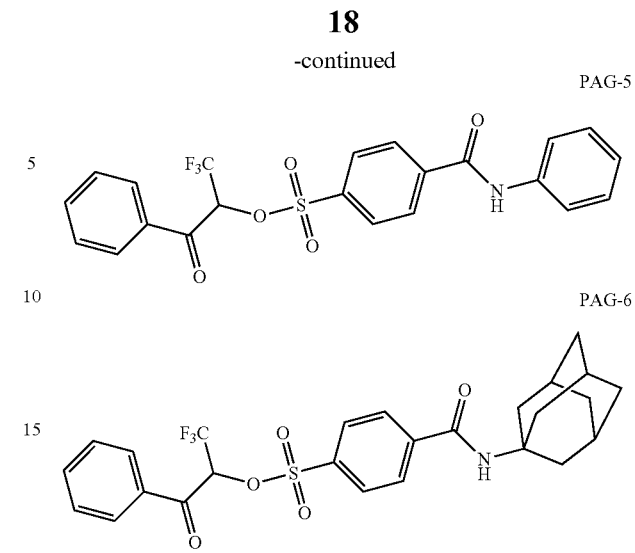

The strong hydrogen bond forming amide functionality adjacent to $R^2$ limits diffusion of the photo-generated acid. The examples further below demonstrate that hydrolytic stability of the PAG can be increased by the introduction of electron donating and/or bulky groups in the ortho position (carbons 2 and/or 6) and para positions (carbon 4) of the aryl ketone group and/or by utilizing a polycyclic aryl ketone group in place of the monocyclic aryl ketone group.

Preparation of PAGs

A method of forming the PAG compounds is illustrated by the reaction of an alpha-hydroxy aryl ketone of formula (6) with an active sulfonate ester of formula (7) (Scheme 10).

Scheme 10

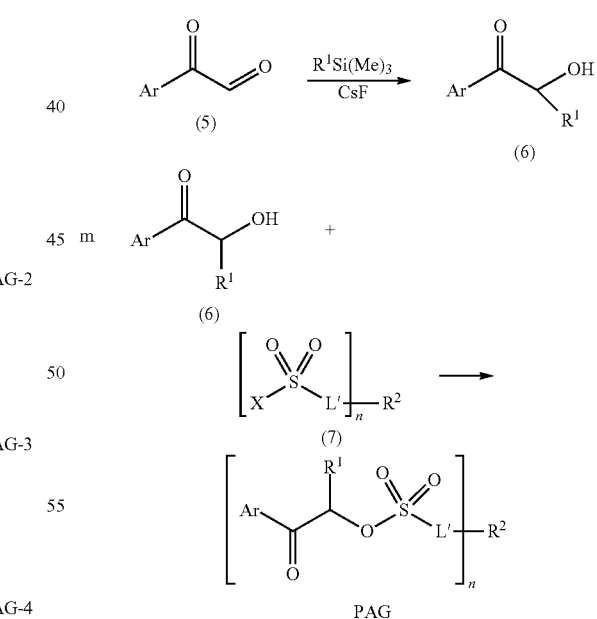

m = n molar equivalents
n = 1, 2, 3, 4
n = 1, 2, 3, 4

Ar, $R^1$, and $R^2$ of Scheme 10 have the same meanings discussed further above. X is an active leaving group (e.g., a halide such as fluoride, chloride, bromide, or iodide). Preferably, X is fluoride or chloride.

In a first step, an aryl glyoxal compound of formula (5) is treated with a fluorinated silane of formula $R^1Si(Me)_3$ to form an alpha-hydroxy aryl ketone of formula (6), thereby introducing perfluorinated group $R^1$. This reaction is catalyzed by CsF. In a second step, the alpha-hydroxy ketone of formula (6) is treated with an activated sulfonyl compound of formula (7), thereby forming the PAG compound.

Non-limiting aryl glyoxal compounds of formula (5) include those of Scheme 11.

Scheme 11

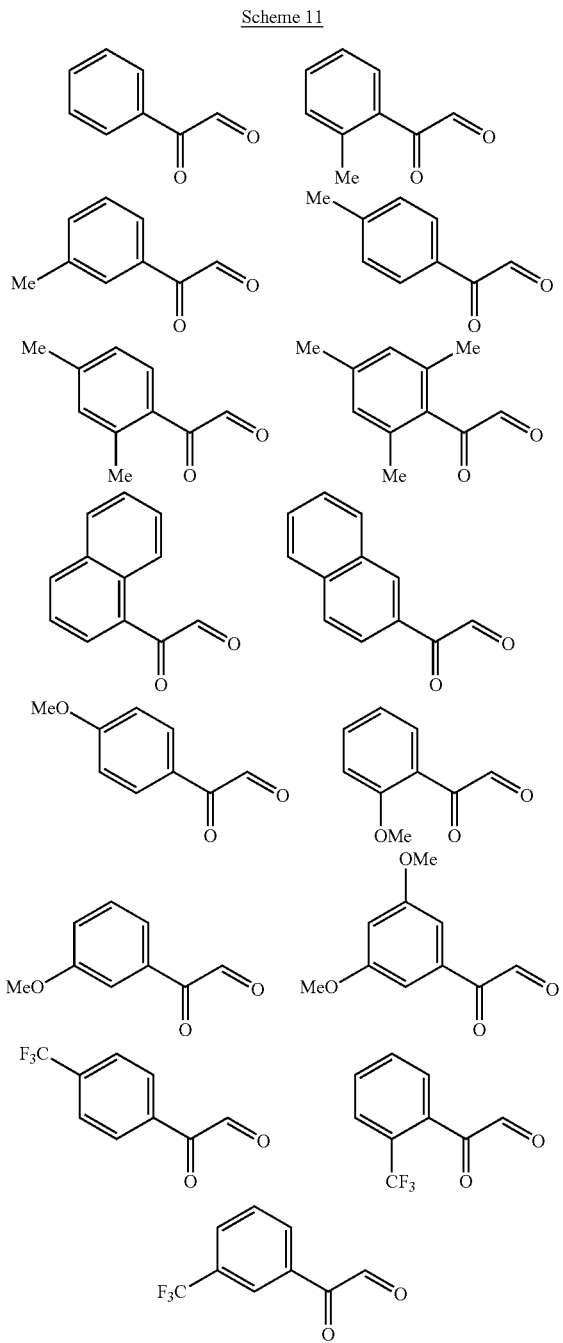

Examples of fluorinated silanes include (trifluormethyl)trimethylsilane, (pentafluorethyl)trimethylsilane, (heptafluoro-n-propyl)trimethylsilane, (nonafluoro-n-butyl)trimethylsilane, (perfluoroisobutyl)trimethylsilane, (perfluoro-n-pentyl)trimethylsilane, and (perfluoroisopentyl)trimethylsilane.

Activated sulfonyl compounds of formula (7) can have any suitable structure within the limitations of the PAG discussed above. Activated sulfonyl compounds used in the examples further below are listed in Scheme 12. It should be understood that many more are commercially available and/or can be prepared by established methods in the art.

Scheme 12

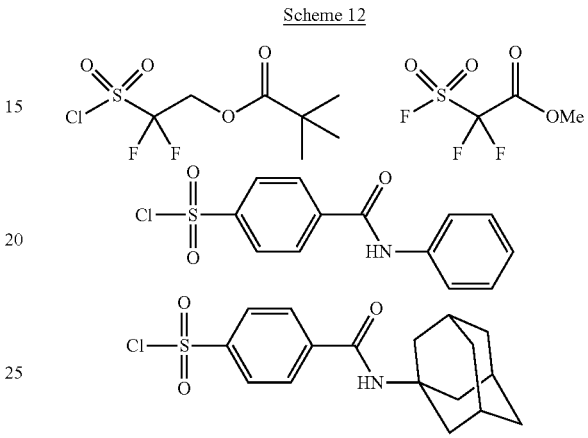

A more specific method of forming the PAG compounds is illustrated in Scheme 13.

Scheme 13

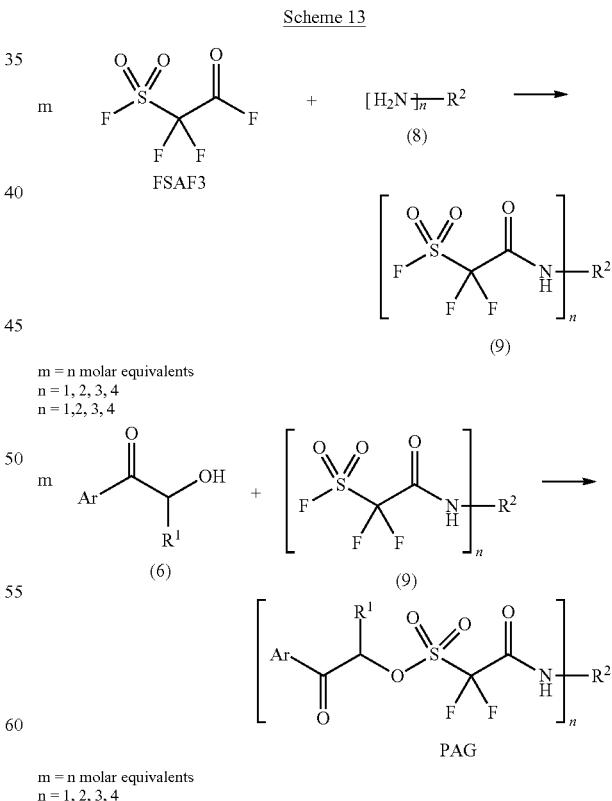

Ar, $R^1$, and $R^2$ of Scheme 13 have the same meanings discussed further above.

In the first reaction of Scheme 13, 2-(fluorosulfonyl) difluoroacetyl fluoride (FSAF3) is treated with an amine [H$_2$N]n-R$^2$ (n=1, 2, 3, or 4 of formula (8)), thereby forming a sulfonyl fluoride compound of formula (9). The molar equivalents of FSAF3 used in the reaction corresponds to n of formula (8). For example, 2 molar equivalents of FSAF3 are used per equivalent of a diamine of formula (8), where n=2. Under suitable conditions demonstrated by the examples below, the amine compound can preferentially react at the carboxylic acid halide site of the bis-acid halide FSAF3, forming the intermediate amide sulfonyl halide compound of formula (9). This reaction is preferably conducted at a temperature of about 0° C. The amide sulfonyl halide compound of formula (9) is then treated with the alpha-hydroxy aryl ketone of formula (6), thereby forming the PAG compound.

Non-limiting examples of amines of formula (8) include those of Scheme 14.

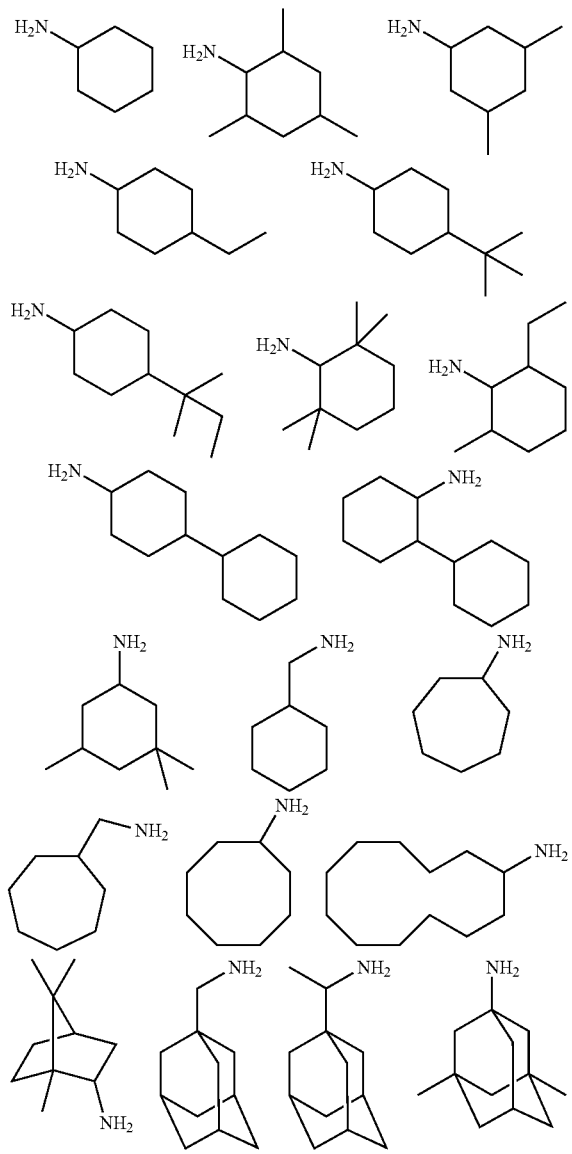

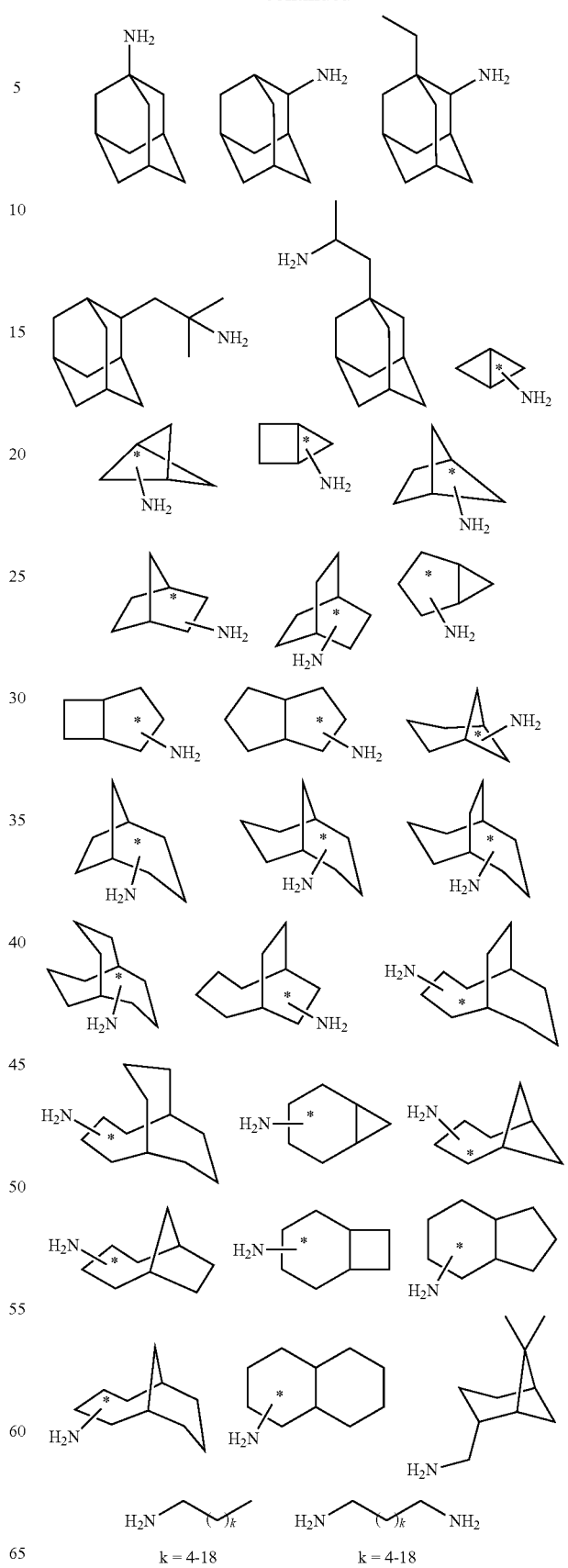

-continued
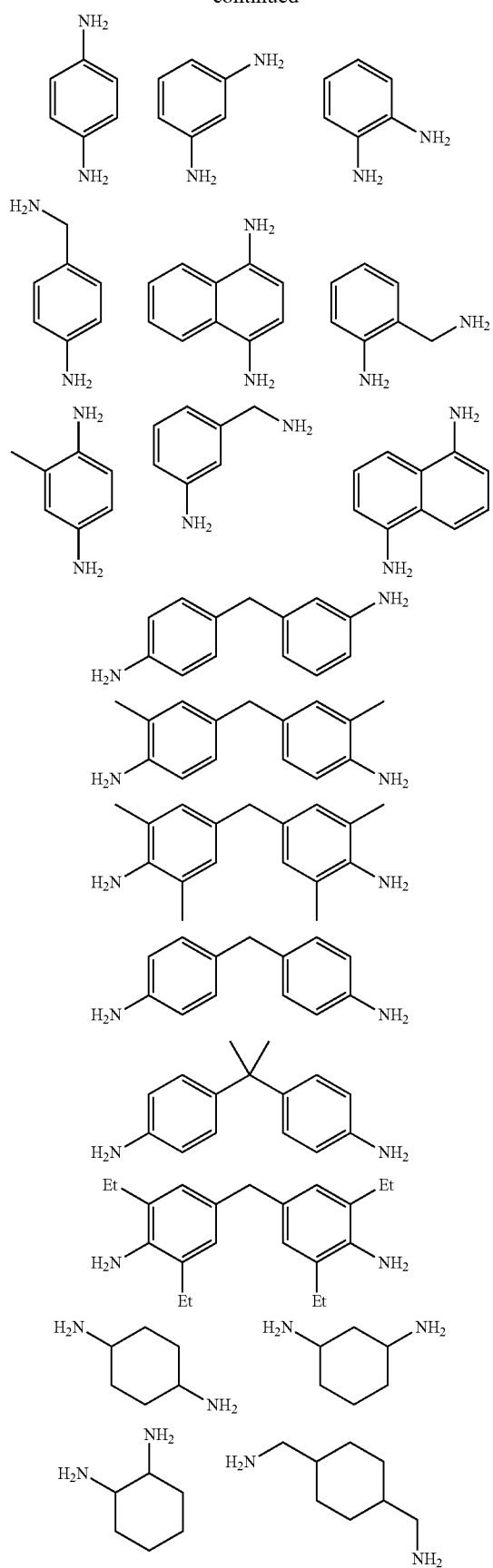
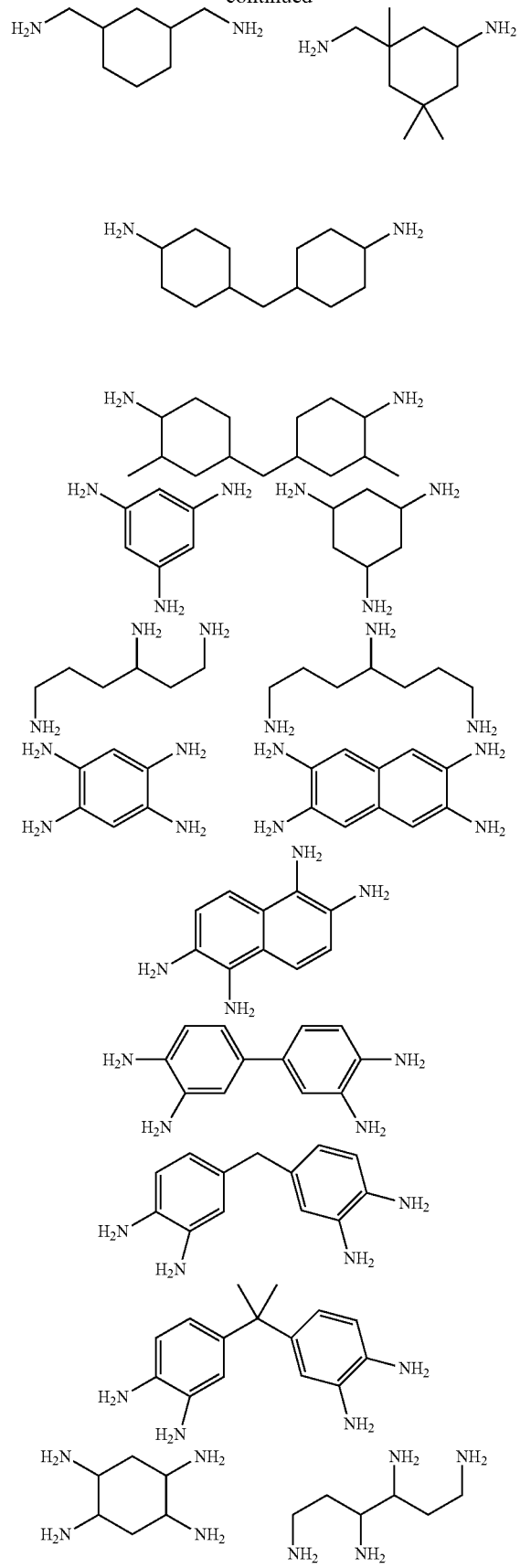

Other amine compounds include silsesquioxanes of formula (10):

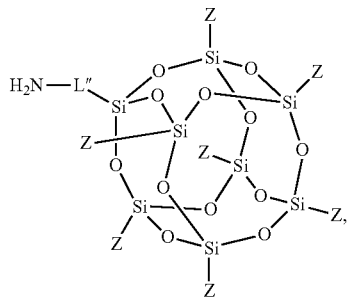

(10)

wherein
L" is a divalent $C_1$-$C_6$ linking group, and
Z is a $C_1$-$C_6$ alkyl group.

More specific silsesquioxanes include the following POSS® compounds sold by Hybrid Plastics of Hattiesburg Miss., USA, where Z is isobutyl (*—$CH_2CH(CH_3)_2$).

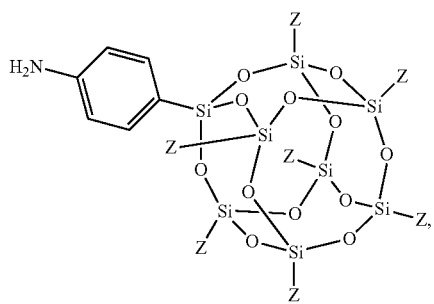

AminophenylisobutylPOSS

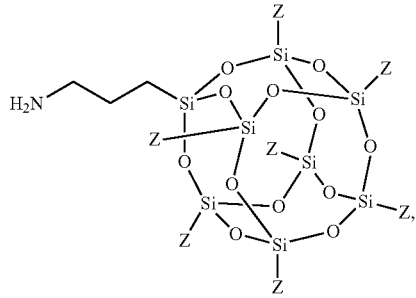

aminopropylisobutylPOSS

In an embodiment, the amine is a compound selected from the group consisting of phenylamine, 1-adamantylamine, 1,6-hexanediamine, aminopropylisobutylPOSS, and aminophenylisobutylPOSS.

Non-limiting exemplary solvents for the above reactions include dichloromethane, chloroform, toluene, diethyl ether, carbon tetrachloride, 1,2-dichloroethane, tetrachloroethylene, chlorobenzene, dimethylformamide and acetonitrile. The solvents can be used singularly or in combination.

Resist Formulation

The PAG compound is used in a resist formulation (composition) in the form of a solution mixed with other components. When the PAG compound is used with a resin, the resin can be a positive tone resin or a negative tone resin. Non-limiting exemplary resins include polymers, molecular glasses, organometallic complexes, oligomers, and the like.

The resist composition can include not only a solvent but also various additives commonly used for resist compositions such as, for example, an auxiliary resin, a quencher, a dissolution inhibitor, a plasticizer, a stabilizer, a coloring agent, a surfactant, a viscosity improver, a leveling agent, an antifoaming agent, a compatibilizer, a primer, and/or an antioxidant. In the case of the negative resist composition, other additives such as a crosslinking agent and/or a basic compound can further be added. The additives can be used in addition to the following materials.

Resin

The resin can contain an acid-labile group so as to perform a positive resist function, or a cross-linking functionality so as to perform a negative resist function.

Examples of resins for a positive resist composition are those comprising a repeat unit having a pendant carboxyl group or acidic hydroxyl group protected by an acid-labile group on a side chain thereof, and a main chain portion derived from a polymerization of a vinyl polymerizable group, such as a repeat unit formed by polymerization of acrylic acid, methacrylic acid, α-trifloromethylacrylic acid, a vinyl group, an allyl group, and/or norbornene group.

Examples of the resin for the negative resist composition are those comprising a repeat unit having a cross-linking functionality on a side chain thereof such as, for example, hydroxyl groups, carboxyl groups, oxiranes (epoxides), oxetanes, blocked isocyanates, and a main chain portion resulting from a polymerization of a vinyl polymerizable group, such as a repeat unit formed by polymerization of acrylic acid, methacrylic acid, α-trifloromethylacrylic acid, vinyl group, allyl group, and/or norbornene group. The cross-linking functionalities can be present singularly or in combination.

The resin generally has a number average molecular weight of 1,000 to 1,000,000, preferably 2,000 to 500,000, as measured by gel permeation chromatography (GPC). If the number average molecular weight of the resin is less than 1,000, the resulting resist composition generally does not form a film with sufficient strength. If the number average molecular weight of the resin exceeds 1,000,000, the solubility of the resin in the solvent decreases, adversely affecting the uniformity of films formed with the resist composition. The molecular weight distribution (Mw/Mn, PDI) of the resin is preferably in the range of 1.01 to 3.00, most preferably 1.10 to 2.50.

Crosslinking Agents

Non-limiting exemplary cross-linking agents for a negative resist composition, include compounds formed by reacting an amino-containing compound (e.g., melamine, acetoguanamine, benzoguanamine, urea, ethylene urea, propylene urea, and glycoluril) with formaldehyde or a mixture of formaldehyde and lower alcohol, thereby substituting a hydrogen atom of the amino group with a hydroxymethyl group or a lower alkoxymethyl group. Herein, the cross-linking agents using melamine, urea, alkylene urea (e.g., ethylene urea, propylene urea, and the like) and glycoluril are hereinafter referred to as "melamine-based cross-linking agent", "urea-based cross-linking agent", "alkylene urea-based cross-linking agent" and "glycoluril-based cross-linking agent", respectively. The cross-linking agent is preferably at least one selected from the group consisting of melamine-based cross-linking agents, urea-based cross-linking agents, alkylene urea-based cross-linking agents and glycoluril-based cross-linking agents. Particularly preferred are glycoluril-based cross-linking agents.

Examples of the melamine-based cross-linking agents are hexamethoxymethylmelamine, hexaethoxymethylmelamine, hexapropoxymethylmelamine and hexabutoxymethylmelamine. Hexamethoxymethylmelamine is preferred.

Examples of the urea-based cross-linking agents are bismethoxymethylurea, bisethoxymethylurea, bispropoxymethylurea and bisbutoxymethylurea. Bismethoxymethylurea is preferred.

Examples of the alkylene urea-based cross-linking agents are: ethylene urea-based cross-linking agents such as mono- and/or di-hydroxymethylated ethylene urea, mono- and/or di-methoxymethylated ethylene urea, mono- and/or di-ethoxymethylated ethylene urea, mono- and/or di-propoxymethylated ethylene urea and mono- and/or di-butoxymethylated ethylene urea; propylene urea-based cross-linking agents such as mono- and/or di-hydroxymethylated propylene urea, mono- and/or di-methoxymethylated propylene urea, mono- and/or di-ethoxymethylated propylene urea, mono- and/or di-propoxymethylated propylene urea and mono- and/or di-butoxymethylated propylene urea; 1,3-di(methoxymethyl)-4,5-dihydroxy-2-imidazolidinone; and 1,3-di(methoxymethyl)-4,5-dimethoxy-2-imidazolidinone.

Examples of the glycoluril-based cross-linking agents are mono-, di-, tri- and/or tetra-hydroxymethylated glycoluril, mono-, di-, tri- and/or tetra-methoxymethylated glycoluril, mono-, di-, tri- and/or tetra-ethoxymethylated glycoluril, mono-, di-, tri- and/or tetra-propoxymethylated glycoluril and mono-, di-, tri- and/or tetra-butoxymethylated glycoluril.

The total amount of the cross-linking agent used is preferably 3 to 30 parts by mass, more preferably 3 to 25 parts by mass, most preferably 5 to 20 parts by mass, per 100 parts by mass of the resin of the resist composition. If the total amount of the cross-linking agent is less than 3 parts by mass of the resin, the resist composition is generally not capable of sufficient cross-linking to form a desirable resist pattern. The resist composition can exhibit poor storage stability and/or deteriorate in sensitivity with time if the total amount of the cross-linking agent exceeds 30 parts by mass of the resin.

Basic Compounds

The basic compound is preferably contained as an optional component in the resist composition so as to function as a quencher or to obtain improvements in resist pattern shape and post exposure stability.

Exemplary basic compounds include primary, secondary and tertiary aliphatic amines, aromatic amines, heterocyclic amines, nitrogen-containing compounds with hydroxyphenyl group, alcoholic nitrogen-containing compounds and amide derivatives. Other basic compounds include tetralkylammonium hydroxides (e.g., tetraoctylammonium hydroxide). Secondary and tertiary aliphatic amines, aromatic amines and heterocyclic amines are preferred. The amine N—H group can optionally be protected by a tert-butyloxycarbonyl group (t-BOC group).

The aliphatic amines can be in the form of alkylamines or alkylalcoholamines each obtained by replacing at least one hydrogen atom of ammonia ($NH_3$) with a $C_1$-$C_{12}$ alkyl or hydroxyalkyl group. Examples of the aliphatic amines are: monoalkylamines such as n-hexylamine, n-heptylamine, n-octylamine, n-nonylamine and n-decylamine; dialkylamines such as diethylamine, di-n-propylamine, di-n-heptylamine, di-n-octylamine and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine and tri-n-dodecylamine; and alkylalcoholamines such as diethanolamine, triethanolamine, diisopropanolamine, triisopropanolamine, di-n-octanolamine and tri-n-octanolamine. Above all, alkylacoholamines and trialkylamines are preferred. More preferred are alkylalcoholamines. Among the alkylalcoholamines, triethanolamine and triisopropanolamine are particularly preferred.

Other examples of the basic compound are: aromatic or heterocyclic amines including aniline, aniline derivatives such as N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline and N,N-dimethyltoluidine, heterocyclic amines such as 1,5-diazabicyclo[4.3.0]non-5-ene, 1,8-diazabicyclo[5.4.0]undec-7-ene, 1,4-diazabicyclo[2.2.2]octane, 4-dimethylaminopyridine, hexamethylenetetramine and 4,4-dimethylimidazoline, and hindered amines such as bis(1,2,2,6,6-pentamethyl-4-piperidyl)sebacate; and alcoholic nitrogen-containing compounds such as 2-hydroxypyridine, aminocresol, 2,4-quinolinediole, 3-indole methanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, and 2-phenyl benzimidazole. The basic compounds can be used singularly or in combination.

The amount of the basic compound used is generally 0.01 to 5 parts by mass per 100 parts by mass of the resin of the resist composition.

Acid Additives

In the case of the negative resist resin, an organic carboxylic acid, a phosphorus oxo acid, and/or a derivative thereof can be added as an optional component in order to prevent sensitivity deterioration caused by the addition of the basic compound and to obtain improvements in resist pattern shape and post exposure stability. This acid compound can be used singularly or in combination with the basic compound.

Exemplary organic carboxylic acid include malonic acid, citric acid, malic acid, succinic acid, benzoic acid and salicylic acid.

Examples of phosphorus oxo acid and its derivatives are: phosphoric acids and ester derivatives thereof, such as phosphoric acid, di-n-butyl phosphate and diphenyl phosphate; phosphonic acids and ester derivatives thereof, such as phosphonic acid, dimethyl phosphonate, di-n-butyl phosphonate, phenylphosphonic acid, diphenyl phosphonate and dibenzyl phosphonate; and phosphinic acids or ester derivatives thereof, such as phosphinic acid and phenylphosphinic acid. Phosphonic acid is particularly preferred.

Solvents

There is no particular limitation on the organic solvent as long as the PAG compound can be dissolved in the organic solvent. Non-limiting organic solvents include: ketones such as acetone, methyl ethyl ketone, cyclohexanone, methyl isoamyl ketone and 2-heptanone; polyhydric alcohols and derivatives thereof, such as monomethyl ether, monoethyl ether, monopropyl ether, monobutyl ether or monophenyl ether of ethylene glycol, ethylene glycol monoacetate, diethylene glycol, diethylene glycol monoacetate, propylene glycol, propylene glycol monoacetate, propylene glycol monomethyl ether, propylene glycol monomethyl etheracetate (PGMEA), dipropylene glycol or dipropylene glycol monoacetate; cyclic ethers such as dioxane; esters such as methyl lactate, ethyl lactate, methyl acetate, ethyl acetate, butyl acetate, methyl pyruvate, ethyl pyruvate, methyl methoxypropionate and ethyl ethoxypropionate; aromatic solvents such as xylene and toluene; lactones such as gamma-butyrolactone; and fluorinated solvents such as fluorocarbon, hydrofluorocarbon, perfluoro compound and hexafluoroisopropyl alcohol. There can also be used a high-boiling-point weak solvent such as turpentine-based petroleum naphtha solvent or paraffin solvent for improvement in ease of application. These solvents can be used singularly or in combination.

Surfactants

Non-limiting surfactants for the resist composition include one or more fluorine- and/or silicon-based surfactants (i.e., fluorine-based surfactant, silicon-based surfactants, and surfactant containing both of fluorine and silicon atoms).

A resist composition comprising a surfactant is generally effective for use with an exposure light source of 250 nm or less wavelength, notably 220 nm or less wavelength and for pattern formation with a narrower pattern line width. It is possible to attain good sensitivity and resolution and obtain good resist patterning with less adhesion/development failures.

Other Acid Generators

The PAG compounds can be used singularly or in combination. The amount of the PAG compound used, including any second acid generating material, is generally in the range of 0.5 to 20 parts by mass per 100 parts by mass of the resist composition. If the amount of the acid generator is less than 0.5 parts by mass, the resist composition is generally not effective in forming good resist patterns. Moreover, storage stability of the resist composition decreases. The PAG compound is generally used in an amount of 1 to 100 parts by mass, preferably 10 to 100 parts by mass, more preferably 30 to 100 parts by mass, per 100 parts by mass of the total acid generator content.

Additive Resins

The resin composition can include one or more auxiliary resins in addition to the resin. There is no particular limitation placed on the auxiliary resin as long as the auxiliary resin can be dissolved in the solvent used and has compatibility with the other components of the resist composition. The auxiliary resin can function as an in-situ top coat, a plasticizer, a stabilizer, as a viscosity improver, a leveling agent, an antifoaming agent, a compatibilizer, and/or a primer.

Pattern Formation Method

Pattern formation using the resist composition can be performed by well-known lithographic processes. The process generally involves coating, prebaking, exposing to high-energy radiation (typically E-Beam, deep ultraviolet (DUV, e.g., 248 nm, 193 nm), or extreme ultraviolet (EUV, e.g., 13.5 nm), post exposure baking (PEB), and developing with alkaline developer. These steps are described in more detail below.

The term "substrate" refers to all underlying layers of a structure on which the resist layer is disposed. The term "disposed" refers to a layer in contact with a surface of another layer. "Disposing" or "applying" refer to forming a layer to be in contact with a surface of another layer, without limitation as to the method employed unless otherwise stated, providing the desirable properties of the disposed or applied layer are not adversely affected (e.g., uniformity and thickness). The term "casting" refers to forming a layer of a material by disposing a solution of the material dissolved in a solvent on a surface of another layer, and removing the solvent.

The substrate can have one or more layers arranged in a stack. The substrate, and more particularly the surface of the substrate, can comprise inorganic or organic materials such as metals, carbon, or polymers. The terms "surface" or "underlying surface" refer to the substrate surface on which the resist layer is disposed. More particularly, the substrate and/or surface of the substrate can comprise an inorganic material and/or organometallic material such as, for example, Si, SiGe, SiGeC, SiC, $SiO_2$, SiN, SiON, SiOC, TiN, WSi, BPSG, SOG, Ge alloys, GaAs, InAs, InP, as well as other III-V or II-VI compound semiconductors. The inorganic material and/or organometallic material can be doped, undoped or contain both doped and undoped regions therein. The substrate can also comprise a layered semiconductor such as Si/SiGe, or a semiconductor-on-insulator (SOI). In particular, the substrate can contain a Si-containing semiconductor material (i.e., a semiconductor material that includes Si) such as, for example, silicon dioxide, silicon nitride, and quartz. A more particular surface layer comprises Cr, CrO, CrON, MoSi, and the like.

In a multi-layered substrate, the layer directly below and in contact with the resist layer is the top-most layer of the substrate, also referred to as "the underlayer" to the resist layer. As non-limiting examples, the resist layer can be disposed on the surface of a silicon wafer or a metal foil, or more particularly on the surface of an anti-reflection layer (ARC) of a multi-layer substrate, where the ARC layer is the top-most layer of the substrate. In this example, the ARC layer is also the underlayer of the resist layer. In another example, the ARC layer has a polymer brush layer attached to the top surface. In this example, the polymer brush layer is also the underlayer of the resist layer.

It should be understood that in some cases (e.g., when forming dense, high resolution patterns) all of the resist layer can receive some dose of radiation exposure. "Non-exposed resist" refers to resist that has received an insufficient dose to switch the solubility of the resist in a given developer compared to the pre-exposed resist (including pre-exposed resist that has been treated with an optional bake and/or optional rinse). "Exposed resist" has received sufficient exposure to switch the solubility of the resist in a given developer compared to the pre-exposed resist.

"Polarity change" implies an altered chemical composition that affects relative solubility without crosslinking. The extent of the polarity change can be measured by comparing the solubility of the exposed resist and non-exposed resist in a given developer. "Inducing a polarity change" in the resist layer means subjecting the resist layer to a treatment involving exposure, a post-exposure bake (PEB) and/or an optional rinse that alters the chemical composition of the layer such that the treated resist has a different solubility compared to the pre-treated resist in a given developer (e.g., tetramethylammonium hydroxide (TMAH) solution in water).

Figure 1B:
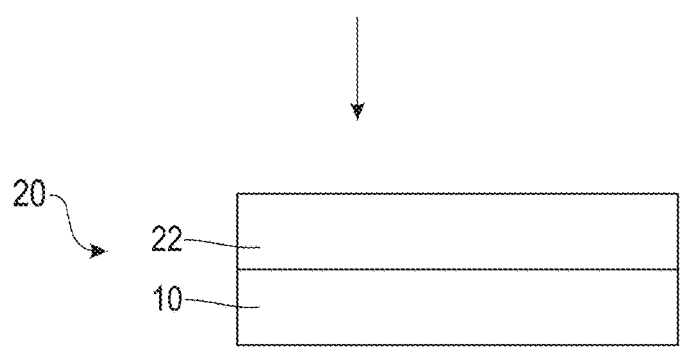

In the following example, the resin is capable of chemical amplification by formation of acid groups. In this instance, a positive-tone lithographic pattern can be formed, as illustrated in the schematic layer diagrams of FIGS. 1A to 1E. A resist composition comprising at least the resin, PAG compound, base quencher, and a solvent is disposed on surface 12 of substrate 10 (FIG. 1A) using any suitable coating technique (e.g., spin casting) followed by removal of the solvent to form resist layer 22 of structure 20 (FIG. 1B). Resist layer 22 comprises the solid components of the resist composition.

Resist layer 22 can be treated with an optional post-application bake (PAB) and/or an optional solvent rinse under suitable conditions of time and temperature before pattern-wise exposure. The optional PAB treatment is typically performed at a temperature of 50° C. to 250° C. for a period of 1 second to 10 minutes, more specifically 90° C. to 130° C. for about 1 minute. The PAB can be used to dry the film of excess solvent, remove unwanted or excess organic ligand, and/or partially crosslink the resist layer. The thermally treated dry film typically will have a thickness of 0.01 micrometers to 10 micrometers, depending on the subsequent radiation source and the desired application.

Figure 1C:
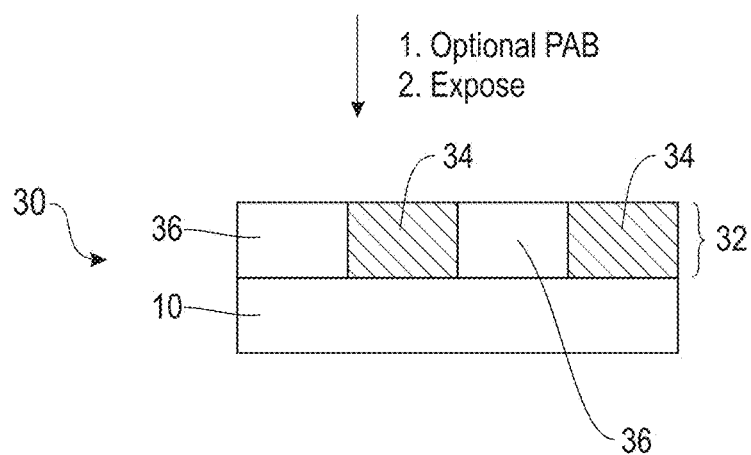

Then, the resist film is exposed to high-energy radiation, such as deep ultraviolet (DUV) light, excimer laser, x-ray, or extreme ultraviolet (EUV) light through a mask having a desired pattern. Pattern-wise exposure of resist layer 22 to high energy radiation results in exposed resist layer 32 of structure 30 (FIG. 1C). An ultraviolet light exposure dose is preferably on the order of about 1 $mJ/cm^2$ to about 200 $mJ/cm^2$, more preferably about 10 $mJ/cm^2$ to about 100 $mJ/cm^2$. The exposure can be performed by conventional lithography or by liquid immersion lithography. The liquid immersion exposure device uses a medium such as water, a hydrocarbon liquid, and/or a fluorinated liquid between the mask and the resist film in the optical path, which causes less absorption of high energy radiation and enables more efficient fine processing in terms of numerical aperture and effective wavelength. In this case, a protective film that is insoluble in water can be applied beforehand to the resist film. Alternatively, a pattern can be written on the resist film directly with an electron beam (e-beam), in which case the exposure dose is generally in the range of about 1 $\mu C/cm^2$ to about 400 $\mu C/cm^2$.

Exposed resist layer 32 is composed of regions of exposed resist 34 and regions of non-exposed resist 36. Exposed resist layer 32 can be treated with an optional post-exposure bake (PEB) and/or an optional solvent rinse under suitable conditions of time and temperature before development. The optional PEB can be performed at a temperature of 50° C. to 150° C. for 1 second to 10 minutes, more specifically 80° C. to 140° C. for about 1 to 5 minutes.

The resist layer can be rinsed before or after the exposure, the PAB, and/or the PEB with a solvent (e.g., water, aqueous solutions, including water/alcohol mixtures, and organic solvents). Typically, a rinse is performed after the PAB. Rinses can be performed at or near room temperature (e.g., 10° C. to 50° C.) for a period of 1 second to 1 hour. The optional baking (PAB and/or PEB) treatments and/or optional rinsing treatments can enhance the solubility difference of the exposed resist compared to the non-exposed resist. A PAB and/or PEB can facilitate deprotection of acid sensitive protecting groups and/or elimination of reaction byproducts of the resist composition.

Figure 1D:
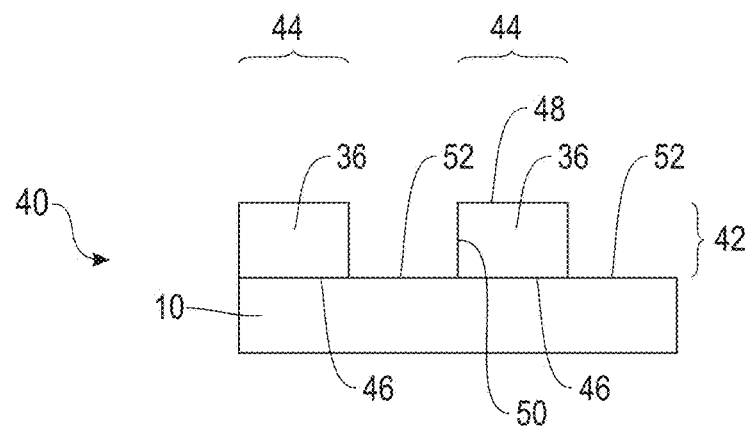

The exposed resist 34 and/or baked exposed resist 34 has greater solubility in an aqueous alkaline developer compared to non-exposed resist 36. Consequently, aqueous alkaline development of the exposed resist layer affords a positive-tone image by removing regions of exposed resist 34. Typically, the developer is 0.1 to 5 wt %, preferably 2 to 3 wt % aqueous solution of tetramethylammonium hydroxide (TMAH), and the development time is for 0.1 to 3 minutes, preferably 0.5 to 2 minutes. Development can be conducted by conventional techniques such as dip, puddle and spray techniques, resulting in layered structure 40 comprising patterned resist layer 42 (FIG. 1D). Patterned resist layer 42 is a topographical relief pattern comprising resist features 44 composed of non-exposed resist 36. Resist features 44 are disposed on surface 46 of substrate 10 and have top surface 48 and sidewall 50. Substrate surface 52 is in contact with air.

Optionally, the pre-developed resist layer and/or post-developed resist layer can be treated with water vapor and/or alcohol vapor either at room temperature or at elevated temperature on a time scale of 1 minute to 5 hours. Such a treatment after exposure and PEB can be conducted, for example, to promote deprotection of acid sensitive groups by acid-catalyzed hydrolysis (e.g., the deprotection of acetal-based protecting groups).

Figure 1E:
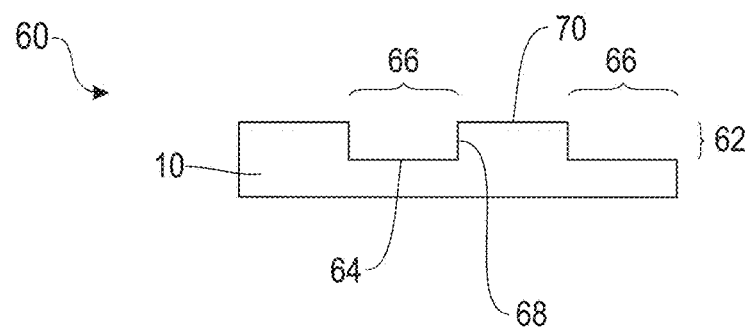

The topographical relief pattern of patterned resist layer 42 can be transferred to substrate 10 by known methods followed by removal of resist features 44 (e.g., oxygen ion etching), resulting in structure 60 (FIG. 1E). Structure 60 comprises a transferred topographical pattern 62 within substrate 10, whose features 66 comprise bottom surface 64, sidewall surface 68, and top surface 70 of substrate 10.

Developers

The aqueous alkaline developer for positive tone development can comprise any suitable base. Non-limiting exemplary bases include sodium hydroxide, potassium hydroxide, sodium carbonate, and various tetraalkylammonium hydroxides such as, for example, tetramethylammonium hydroxide (TMAH) and tetrabutylammonium hydroxide (TBAH). The aqueous alkaline developer can comprise one or more bases. Preferably, the aqueous alkaline developer comprises a tetraalkylammonium hydroxide, more preferably tetramethylammonium hydroxide. Preferably, the TMAH developer comprises 0.1 to 5 wt % tetramethylammonium hydroxide (TMAH) based on total weight of the developer solution in water.

The organic solvent developer for negative tone development can comprise any suitable organic solvent. Non-limiting exemplary organic solvents include ketone-based solvents, ester-based solvents, alcohol-based solvents, amide-based solvents, ether-based solvents, and hydrocarbon-based solvents. More specific organic solvent developers include methyl benzoate (MeB), ethyl 3-ethoxypropionate (EEP), 2-heptanone (MAK), 4-methyl-2-pentanone (4M2P), n-butyl acetate (NBA), amyl acetate, propylene glycol methyl ether acetate (PGMEA), anisole, acetophenone, and combinations thereof.

Post-Development Treatment

The patterned resist layer can also be given a post-development treatment, for example, to increase etch resistance. The post-development treatment can be photochemical, thermal, chemical, or a combination thereof. As an example, the patterned resist layer can be given a second exposure to a second radiation, thereby forming a treated patterned resist layer. The second exposure can be performed with a single wavelength of second radiation or a combination of suitable wavelengths (broad band) of second radiation, so long as the exposure is effective in inducing the desired response of the treated patterned resist layer. The second exposure treatment can be a flood exposure. The flood exposure can be a single conventional whole area exposure or a combination of conventional whole area exposures. The exposure treatment can also be a scanning exposure delivered by a digital writing device employing light emitting sources. The second exposure can be followed by a thermal treatment to chemically amplify the formation of chemical functional groups in the treated patterned resist layer. For example, the flood exposure can release an acid from previously unreacted photo-acid generator (PAG) that upon subsequent heating catalyzes the deprotection of additional acid-sensitive carboxylic acid esters, aromatic acetals/ketals, and/or carbonates, thereby increasing the concentration of carboxylic acid and phenol groups in the treated patterned resist layer. With sufficient polarity change, the treated patterned resist layer can be rendered insoluble in either a low polarity solvent (e.g., anisole) or a more polar organic solvent, while retaining solubility in aqueous alkaline developer and/or a second organic solvent, without crosslinking the resist.

A post-development thermal treatment can further tailor the solvent compatibility, chemical structure of the resist material, and/or etch resistance of the patterned resist layer.

Intermediate layer 76 can be, for example, an ARC layer. In this example, surface 78 is a surface of the ARC layer in contact with air, and resist features 44 are disposed on ARC surface 80.

The following examples demonstrate the preparation of the PAG compounds, resist compositions thereof, and resist patterns formed therefrom. The resist formulations were not optimized.

EXAMPLES

Commercially available materials used in the following examples are listed in Table 1.

TABLE 1

| ABREVIATION | DESCRIPTION | SUPPLIER |
|---|---|---|
| MF-26A | 2.3 Wt % Aqeous Tetramethyl Ammonium Hydroxide Solution (TMAH) | FUJIFILM |
| Quencher 1 | 2-Phenyl Benzimidazole | Sigma-Aldrich |
| FSAF3 | 2-(Fluorosulfonyl)Difluoroacetyl Fluoride | Synquest |
| | 2-Hydroxyacetophenone | Sigma-Aldrich |
| | Aniline | Sigma-Aldrich |
| | 1-Adamantylamine | Sigma-Aldrich |
| | 4-(Chlorosulfonyl)Benzoic Acid | Sigma-Aldrich |
| | Phenylglyoxal hydrate | Sigma-Aldrich |
| | 4,4'-Biphenylsulfonyl Chloride | TCI |
| | Hexamethylenediamine | Sigma-Aldrich |
| | 4-Methoxyacetophenone | Sigma-Aldrich |
| | (Diacetoxyiodo)Benzene | Sigma-Aldrich |
| NBHFAMA | 2-{[5-(1',1',1'-Trifluoro-2'-Trifluoromethyl-2'-Hydroxy)Propyl]Norbornyl]} Methacrylate | Central Glass |
| ECPMA | 1-Ethylcyclopentyl Methacrylate | JSR |
| | 2-Bromo-2,2-Difluoroethyl Pivalate | Central Glass |
| POSS-1 | AminopropylisobutylPOSS ® | Hybrid Plastics |
| | Methyl 2,2-Difluoro-2-(Fluorosulfonyl)Acetate | Sigma-Aldrich |

The thermal treatment can be conducted at a temperature of 50° C. to 600° C., 50° C. to 300° C., or 50° C. to 200° C. for a period of 1 sec to 1 day.

A chemical treatment can include, for example, contacting the patterned resist layer with the vapors of a volatile Lewis acid, such as hydrochloric acid, sulfuric acid, nitric acid, or a sulfonic acid. In each type of treatment, the chemical alteration of the resist is preferentially uniformly distributed throughout the treated resist, not just at the surface. The post-development chemical treatment can cause a chemical change in the revealed surface of the substrate, producing (after removal of the resist features) a chemically patterned surface of the substrate.

Other post development treatments can include infiltration by ALD (aka SIS process) or chemical infiltration methods to infiltrate inorganic components into the resist and improve its etch properties.

Etching includes any common etching technique applied in the manufacture of semiconductor devices, for example, dry-etching such as plasma etching, or wet-etching using selective solvents. Typically, dry etching processes are employed for etching at sub-50 nm dimensions.

Figure 2:
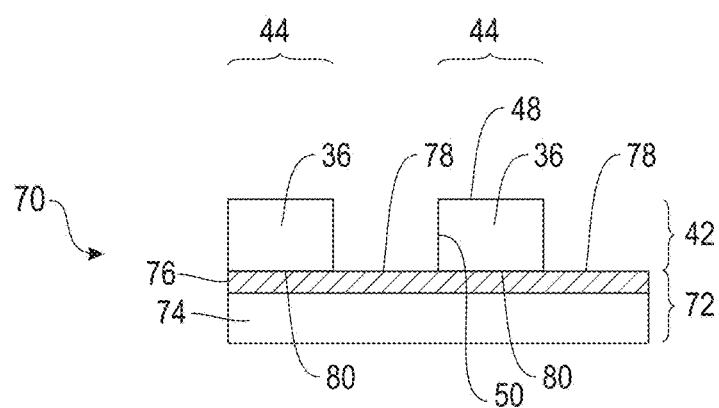
FIG. 2 is a schematic layer diagram of multi-layered structure that includes a topographical patterned layer comprising exposed resist composition disposed on a two layered substrate.

To further illustrate a multi-layered substrate, structure 40 of FIG. 1D is reproduced as structure 70 of FIG. 2, with the exception that substrate 72 of FIG. 2 has two layers, a bottom layer 74 and an intermediate layer 76. Bottom layer 74 of substrate 72 can be, for example, a silicon wafer.

Herein, Mn is the number average molecular weight, Mw is the weight average molecular weight, and MW is the molecular weight of one molecule.

The following examples are intended to provide those of ordinary skill in the art with a complete disclosure and description of how to prepare and use the compositions disclosed and claimed herein. Unless indicated otherwise, parts are parts by weight, temperature is in degrees centigrade (° C.), and pressure is at or near atmospheric pressure. Additionally, all starting materials including the co-monomers other than the PAG monomers were obtained commercially or were synthesized using known procedures.

Where appropriate, the following techniques and equipment were utilized in the examples below: $^1$H NMR and $^{13}$C NMR spectra were obtained at room temperature on an Avance 400 spectrometer. Quantitative $^{13}$C NMR was run at room temperature in acetone-$d_6$ in an inverse-gated $^1$H-decoupled mode using $Cr(acac)_3$ as a relaxation agent on an Avance 400 spectrometer. Thermo-gravimetric analysis (TGA) was performed at a heating rate of 5° C./minute in $N_2$ on a TA Instrument Hi-Res TGA 2950 Thermogravimetric Analyzer. Differential scanning calorimetry (DSC) was performed at a heating rate of 10° C./minute on a TA Instruments DSC 2920 modulated differential scanning calorimeter. Number average and weight average molecular weights were measured in tetrahydrofuran (THF) or dimethylformamide (DMF) on a Waters Model 150 chromatograph relative to polystyrene standards.

In the structures that follow Ph=phenyl, and Ad=1-Adamantyl.

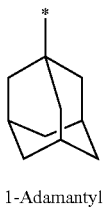 [SMILES: *C12CC3CC(CC(C3)C1)C2]

1-Adamantyl

Resist film layers containing the PAGs were exposed using a 193 nm interferometric tool (IBM Designed NEMO) or a 0.3 NA EUV micro-exposure tool (EUV-MET) at Lawrence-Berkeley National laboratory.

Synthesis of Starting Materials for PAG

Amide-sulfonyl fluoride compounds of Examples 1-4 were prepared using the general reaction shown below, where n=1.

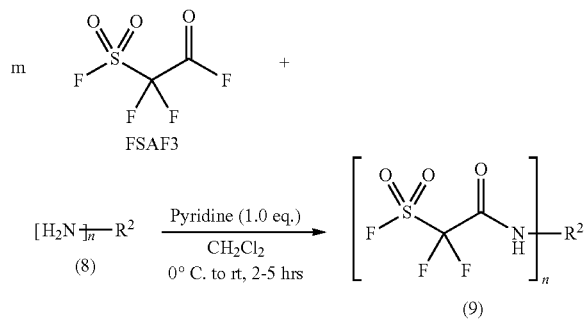

m = n molar equivalents
n = 1, 2, 3, 4
n = 1,2, 3, 4

Example 1. Preparation of SM-1: 1,1-difluoro-2-oxo-2-(phenylamino)ethane-1-sulfonyl fluoride

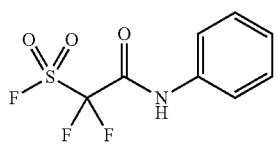

SM-1

A 100 mL flask was charged with CH$_2$Cl$_2$ (10 mL) under nitrogen stream at 0° C. 2-(Fluorosulfonyl)difluoroacetyl fluoride (4.00 g, 22.6 mmol, 1.2 eq.) was added and the mixture was stirred for 5 minutes at 0° C. A solution containing CH$_2$Cl$_2$ (8 mL), aniline (1.71 g, 18.4 mmol, 1.0 eq.), and pyridine (1.45 g, 18.4 mmol, 1.0 eq.) was added dropwise to the mixture over 10 minutes and subsequently the mixture was stirred for an hour at 0° C. In addition, the mixture was allowed to warm to RT and stirred for 4 hours at RT. CH$_2$Cl$_2$ (36 mL) and 1N HCl (18 mL) were added to the final reaction mixture and then the lower layer was separated and washed with 1N HCl (18 mL×2) and brine (18 mL×2). The solution was dried over anhydrous MgSO$_4$ and filtrated and then CH$_2$Cl$_2$ was removed in an evaporator. The target compound was obtained as a pale yellow solid (4.53 g, 97.3% yield). $^1$H-NMR (CDCl$_3$), delta (ppm): 7.35 (tt, J=7.4, 1.1 Hz, 1H), 7.45 (dd, J=7.6, 8.4 Hz, 2H), 7.61 (dd, J=1.0, 8.6 Hz, 2H), 8.08 (brs, 1H). $^{19}$F-NMR (CDCl$_3$, standard: C$_6$F$_6$=−162.2 ppm), delta (ppm): 41.25 (t, J=4.7 Hz, 1F), −105.32 (d, J=4.2 Hz, 2F).

Example 2. Preparation of SM-2: 1,1-Difluoro-2-oxo-2-(1-adamantylamino) ethanesulfonyl fluoride

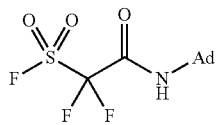

SM-2

A 100 mL flask was charged with C$_2$Cl$_2$ (20 mL) under nitrogen stream at 0° C. and then 2-(fluorosulfonyl)difluoroacetyl fluoride (8.49 g, 47.1 mmol, 1.2 eq.) was added and the mixture was stirred for 10 minutes at 0° C. A CH$_2$Cl$_2$ (20 mL) solution of 1-adamantylamine (5.94 g, 39.3 mmol, 1.0 eq.) and Pyridine (3.10 g, 39.3 mmol, 1.0 eq.) was added drop-wise to the mixture over 15 minutes and subsequently the mixture was stirred for 4 hours at 0° C. to room temperature. CH$_2$Cl$_2$ (40 mL) and 1N HCl (40 mL) were added to the final reaction mixture and then the lower layer was separated and washed with 1N HCl (40 mL) and brine (40 mL). The solution was dried over anhydrous MgSO$_4$ and filtrated and then CH$_2$Cl$_2$ was removed in an evaporator. The target compound as yellow solid (11.77 g) in 96.2% yield was obtained. $^1$H-NMR (CDCl$_3$), delta (ppm): 1.56 (brs, 6H), 2.03 (brs, 6H), 2.13 (brs, 3H), 6.02 (brs, 1H), $^{19}$F-NMR (CDCl$_3$, standard: C$_6$F$_6$=−162.2 ppm), delta (ppm): 40.55 (t, J=4.8 Hz, 1F), −105.02 (d, J=4.9 Hz, 2F).

Example 3. Preparation of SM-3: 2-(chlorosulfonyl)-2,2-difluoroethyl pivalate

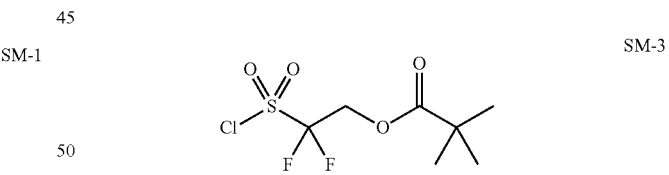

SM-3

A 200 ml flask was charged with 2-bromo-2,2-difluoroethyl pivalate (20.0 g, 81.6 mmol, 1.0 eq.) and MeCN (69 ml) and then a H$_2$O (55 ml) solution of N-benzyl-trimethylammonium chloride (15.9 g, 85.7 mmol, 1.05 eq.) was added thereto and the mixture was stirred for 5 minutes at room temperature. NaHCO$_3$ (20.6 g, 245.0 mmol, 3.0 eq.) and Na$_2$S$_2$O$_4$ (42.6 g, 208.0 mmol, 2.55 eq.) were added to the mixture and then the mixture was allowed to warm to 60-65° C. and stirred for 5 hours. The reaction mixture was allowed to cool to room temperature and the solids were filtered and washed with MeCN (40 ml). The combined filtrate was concentrated in an evaporator and CHCl$_3$ (50 ml) was added to the residue and then the lower layer was separated. The upper layer was extracted with CHCl$_3$ (25 ml) twice and organic layers were combined. CHCl$_3$ was removed in an evaporator and the precursor as white solid (24.9 g) in 80.5% yield was obtained.

A 150 ml flask was charged with the precursor (10.5 g, 27.7 mmol, 1.0 eq.) and $CHCl_3/H_2O$ (28 ml/28 ml) and the mixture was stirred for 10 min at 0° C. N-chlorosuccinimide (7.4 g, 55.3 mmol, 2.0 eq.) was added thereto and the mixture was stirred overnight at 0° C. to room temperature. $CHCl_3$ (56 ml) and $H_2O$ (28 ml) were added to the final reaction mixture and the lower layer was separated and then an upper layer was extracted with $CHCl_3$ (56 ml) twice. After organic layers were combined, the solution was washed with $H_2O$ (28 ml×3) and brine (28 ml). The solution was subsequently dried over anhydrous $MgSO_4$ and $CHCl_3$ was removed in an evaporator. Hexane (20 ml) was added to the crude and a precipitated solid was filtrated and the filtrate was concentrated in an evaporator. The target compound as colorless oil (3.86 g) in 52.7% yield (2 steps: 42.5% yield) was obtained. $^1$H-NMR ($CDCl_3$), delta (ppm): 1.27 (s, 9H), 4.85 (t, J=11.7 Hz, 2H); $^{19}$F-NMR ($CDCl_3$, standard: $C_6F_6$=−162.2 ppm), delta (ppm): −101.60 (t, J=11.7 Hz, 2F)

Example 4. Preparation of SM-4: 1,1-difluoro-2-oxo-2-(aminopropylisobutylPOSS)ethane-1-sulfonyl fluoride

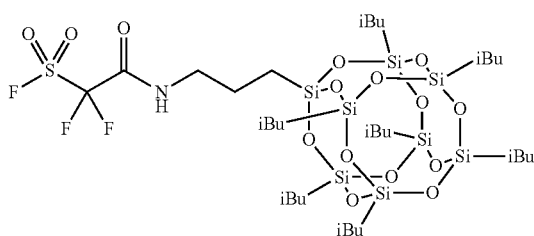

SM-4 iBu = iso-butyl

A 50 ml flask was charged with $CH_2Cl_2$ (15 ml) under nitrogen stream at 0° C. and then 2-(fluorosulfonyl)difluoroacetyl fluoride (5.22 g, 29.0 mmol, 2.0 eq.) was added and the mixture was stirred for 20 minutes at 0° C. A $CH_2Cl_2$ (55 ml) solution of the mixture of aminopropylisobutylPOSS® (POSS-1, 12.7 g, 14.5 mmol, 1.0 eq.) and pyridine (1.15 g, 14.5 mmol, 1.0 eq.) was added drop-wise to this mixture over 40 minutes. The resulting mixture was stirred for 4 hours at 0° C. $CH_2Cl_2$ (70 ml) and 1N HCl (40 ml) were added to the final reaction mixture and then the lower layer was separated and washed with 1N HCl (20 ml×2) and brine (20 ml×2). This solution was dried over anhydrous $Na_2SO_4$ and filtrated and then the $CH_2Cl_2$ was removed in an evaporator. The targeted compound was obtained as white solid (14.4 g, 96.2% yield). $^1$H-NMR ($CDCl_3$), delta (ppm): 2.09 (dd, J=7.1, 1.8 Hz, 14H+2H), 0.98 (d, J=6.6 Hz, 42H), 1.73 (dd, J=6.7, 6.8 Hz, 2H), 1.87 (tsept, J=7.1, 6.6 Hz, 7H), 3.43 (d, J=6.7 Hz, 1H), 3.47 (d, J=6.8 Hz, 1H), 6.56 (s). $^{19}$F-NMR ($CDCl_3$, standard: $C_6F_6$=−162.2 ppm), delta (ppm): 40.51 (t, J=4.8 Hz, 1F), −105.68 (d, J=4.7 Hz, 2F).

Example 5. Preparation of SM-5: 4-(phenylcarbamoyl)benzenesulfonyl chloride

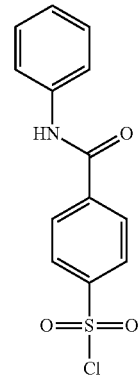

SM-5

Step A. 4-(Chlorosulfonyl)benzoic acid (5 g, 22.7 mmol) was added to a 100 mL round bottom flask that was purged with nitrogen. $SOCl_2$ (20 mL) was added and several drops of dimethylformamide (DMF). The round bottom was then fixed with a Vigreux reflux column, placed in an oil bath and heated to reflux under a constant flow of nitrogen. The reaction mixture was stirred for approximately 1 hour, in which time the solids were observed to be completely dissolved in solution. The solution was then allowed to cool to room temperature and concentrated in-vacuo to give 4-(chlorosulfonyl)benzoyl chloride in quantitative yield. Spectral data of this compound were consistent with previously reported spectral data in the literature (McGeary, R. P., et al., "An 'inside-out' approach to suramin analogues", Tetrahedron (2009), 65(20), 3990-3997).

Step B. To the same round bottom flask from Step A containing 4-(chlorosulfonyl)benzoyl chloride and equipped with a nitrogen inlet was added aniline (2.11 g, 22.7 mmol) and triethyamine (TEA, 3.16 mL, 1 eq.) in dichloromethane (DCM). The solution was cooled to −70° C. using a dry ice acetone bath and stirred a period of 18 hours while allowing the solution to warm to room temperature. The resulting material was then extracted using 1M HCl (2×100 mL) then concentrated and recrystallized from a mixture of hexanes/DCM to give the pure product, 4-(phenylcarbamoyl)benzenesulfonyl chloride.

Example 6. Preparation of SM-6: 4-(((1R,3S,5r,7r)-adamantan-2-yl)carbamoyl)benzenesulfonyl chloride

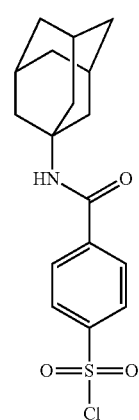

SM-6

Step A. 4-(chlorosulfonyl)benzoyl chloride was prepared in quantitative yield from 4-(chlorosulfonyl)benzoic acid (4.090 g, 18.5 mmol) and $SOCl_2$ (20 mL)/DMF (several drops) as described above in Example 5.

Step B. To the same round bottom flask from Step A containing 4-(chlorosulfonyl)benzoyl chloride and equipped with a nitrogen inlet was added 1-adamantylamine (2.798 g, 18.5 mmol) and TEA (2.6 mL, 1 eq.) in DCM. The solution was cooled to −70° C. using a dry ice acetone bath and stirred for a period of 18 hours while allowing the solution to warm to room temperature. The resulting material was then extracted with 1M HCl (2×100 mL), then concentrated and recrystallized from toluene to give the pure product SM-6.

Example 7. Preparation of SM-7: 2,2'-(hexane-1,6-diylbis(azanediyl)bis(1,1-difluoro-2-oxoethane-1-sulfonyl fluoride)

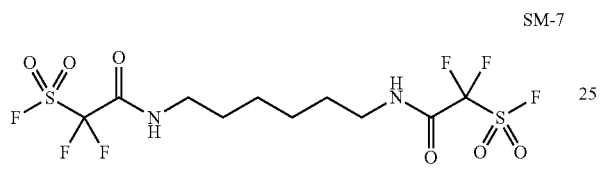

SM-7

A 100 mL flask was charged with $CH_2Cl_2$ (10 mL) under nitrogen stream at 0° C. and then 2-(fluorosulfonyl)difluoroacetyl fluoride (5.82 g, 32.3 mmol, 2.5 eq.) was added and the mixture was stirred for 10 minutes at 0° C. A $CH_2Cl_2$ (15 mL) solution of hexamethylenediamine (1.50 g, 12.9 mmol, 1.0 eq.) and Pyridine (2.04 g, 25.8 mmol, 2.0 eq.) was added drop-wise to the mixture over 10 minutes and the mixture was allowed to warm to RT and stirred for an hour at RT. $Et_2O$ (100 mL) and 1N HCl (20 mL) were added to the final reaction mixture and then the upper layer was separated and washed with 1N HCl (20 mL) and brine (2×20 mL). The solution was dried over anhydrous $MgSO_4$ and filtrated and then solvents were removed in an evaporator. The crude material was purified by recrystallization (3× hexane/$Et_2O$). The target compound as white solid (3.88 g) in 68.9% yield was obtained. $^1$H-NMR (d-Acetone), delta (ppm): 1.37-1.41 (m, 4H), 1.60-1.64 (m, 4H), 3.41 (q, J=6.6 Hz, 4H), 8.97 (brs, 2H). $^{19}$F-NMR (d-Acetone, standard: $C_6F_6$=−162.2 ppm), delta in ppm: 41.51 (dd, J=4.7, 5.1 Hz, 2F), −102.03 (d, J=4.9 Hz, 2F), −102.09 (d, J=4.7 Hz, 2F).

Example 8. Preparation of SM-8: 2,2'-(1,3-phenylenebis(azanediyl))bis(1,1-difluoro-2-oxoethane-1-sulfonyl fluoride)

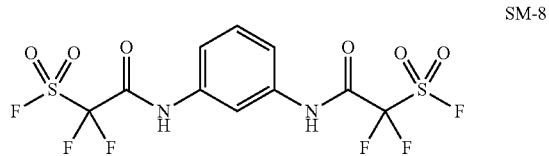 [SMILES: O=C(Nc1cccc(NC(=O)C(F)(F)S(=O)(=O)F)c1)C(F)(F)S(=O)(=O)F]

SM-8

A 100 mL flask was charged with $CH_2Cl_2$ (20.5 ml) under nitrogen stream at 0° C. and then 2-(fluorosulfonyl)difluoroacetyl fluoride (9.39 g, 52.1 mmol, 2.5 eq.) was added and the mixture was stirred for 15 minutes at 0° C. A $CH_2Cl_2$ (11 ml) solution of a mixture of 1, 3-phenylenediamine (2.26 g, 20.8 mmol, 1.0 eq.) and pyridine (3.30 g, 41.7 mmol, 2.0 eq.) was added drop-wise to the reaction mixture over 15 minutes. Subsequently, the mixture was allowed to warm to room temperature (r.t.) and stirred for 4 hours at room temperature. $CH_2Cl_2$ (100 ml) and 1N HCl (50 ml) were added to the final reaction mixture and a solid precipitated. The solid was filtrated and dissolved in $Et_2O$ and the solution was washed with 1N HCl (2×20 mL) and brine (2×20 mL). The solution was dried over anhydrous $Na_2SO_4$, filtered, and the $Et_2O$ was removed in an evaporator. The target compound was obtained as pale yellow solid (8.64 g, 96.7% yield). $^1$H-NMR (d-Acetone), delta (ppm): 7.51 (t, J=8.2 Hz, 1H), 7.65 (dd, J=2.0, 8.2 Hz, 2H), 8.23 (q, J=2.1 Hz, 1H), 10.88 (brs, 2H). $^{19}$F-NMR (d-Acetone, standard: $C_6F_6$=−162.2 ppm), delta (ppm): 42.20 (dd, J=5.8, 4.7 Hz, 2F), −101.59 (d, J=5.2 Hz, 2F), −101.65 (d, J=4.9 Hz, 2F).

Example 9. Preparation of SM-9: 2-hydroxy-2-trifluoromethylacetophenone

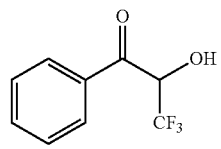

SM-9

A 500 ml flask was charged with phenylglyoxal hydrate (15.21 g, 100 mmol, 1.0 eq.), (trifluoromethyl)trimethylsilane (31.1 g, 205 mmol, 2.05 eq.), and dimethoxyethane (200 mL) under nitrogen stream. The mixture was stirred for 10 minutes at 0° C., after which CsF (280 mg, 2.0 mmol, 0.02 eq.) was added to the mixture in small portions over 10 minutes. The reaction mixture was stirred for 1.5 hours at 0° C. (caution: this reaction has an induction period and is exothermic). Subsequently, the mixture was stirred for 30 minutes at room temperature. THF (20 mL) and 6N HCl (80 mL) were added followed by stirring for 1.5 hours. The upper layer was separated, the lower layer was extracted with $Et_2O$ (100 ml×2), and the organic layers were combined. The organic solution was washed with brine (50 mL), dried over anhydrous $MgSO_4$, and filtered. Solvents were removed in an evaporator and the crude product was purified by column chromatography (hexane/AcOEt) to obtain the target compound as a white solid (2.96 g, 14.5% yield). $^1$H-NMR ($CDCl_3$), delta (ppm): 4.28 (d, J=8.3 Hz, 1H), 5.44 (qd, J=6.6, 8.3 Hz, 1H), 7.58 (dd, J=7.8, 7.9 Hz, 1H), 7.73 (t, J=7.5 Hz, 1H), 8.01 (d, J=7.7 Hz, 1H), $^{19}$F-NMR ($CDCl_3$, standard: $C_6F_6$=−162.2 ppm), delta (ppm): −74.34 (d, J=6.6 Hz, 3F).

PAG Synthesis

Example 10. Preparation of PAG-1

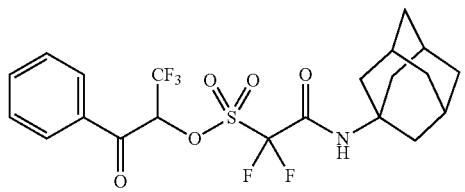

PAG-1

A 100 mL flask was charged with 1,1-difluoro-2-oxo-2-(1-adamantylamino)ethanesulfonyl fluoride (SM-2, 1.01 g, 3.30 mmol, 1.0 eq.), 2-hydroxy-2-trifluoromethylacetophenone (SM-9, 0.64 g, 3.30 mmol, 1.0 eq.) and THF (17 ml) under nitrogen stream and the mixture was stirred for 10 minutes at −50° C. nBuLi (1.6 M, 2.1 mL, 3.30 mmol, 1.0 eq.) was added drop-wise to the mixture over 10 minutes. The mixture was stirred for 4.5 hours while warming from −50° C. to 10° C. 1N HCl (17 mL) was added to the final reaction mixture and then AcOEt (51 mL). The upper layer was separated and the lower layer was extracted with AcOEt (34 mL). The organic solutions were combined and washed with 1N HCl (17 mL) and brine (17 mL). The solution was subsequently dried over anhydrous MgSO$_4$ and filtered. Solvents were removed in an evaporator and the crude product was purified by column chromatography (hexane/AcOEt) to obtain the target PAG as colorless oil to white solid (0.45 g, 27.9% yield). $^1$H-NMR (d-Acetone), delta (ppm): 1.60-1.69 (m, 6H), 2.00 (brs, 3H), 2.81 (brs, 3H), 6.93 (q, J=6.4 Hz, 1H), 7.66 (dd, J=7.4 Hz, 8.2 Hz, 2H), 7.82 (tt, J=1.2, 7.4 Hz, 1H), 8.21 (dd, J=1.3, 8.6 Hz, 2H). $^{19}$F-NMR (d-Acetone, standard: C$_6$F$_6$=−162.2 ppm), delta (ppm): −70.32 (d, J=6.3 Hz, 3F), −101.09 (d, J=244.50, 1F), −102.70 (d, J=244.60, 1F).

Example 11. Preparation of PAG-2

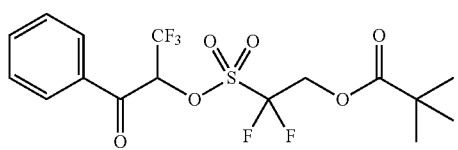

PAG-2

A 25 mL flask was charged with 2-hydroxy-2-trifluoromethylacetophenone (SM-9, 0.57 g, 2.38 mmol, 1.0 eq.) and THF (6 mL) under nitrogen stream, and the mixture was stirred for 15 minutes at −40° C. nBuLi (1.6 M, 1.5 mL, 2.38 mmol, 1.0 eq.) was added drop-wise to the mixture over 10 minutes and the mixture was stirred for 45 minutes at −40° C. This solution was then added drop-wise to a cold (−40° C.) solution of 2-(chlorosulfonyl)-2,2-difluoroethyl pivalate (SM-3, 0.74 g, 2.38 mmol, 1.0 eq.) in THF (6 mL) over 10 minutes. The resulting mixture was stirred for 3 hours while warming from −40° C. to 10° C. 1N HCl (12 mL) was added to the final reaction mixture and then AcOEt (36 mL) was added. The upper layer was separated and the lower layer was extracted with AcOEt (24 mL). The organic layers were combined and washed with 1N HCl (12 mL) and brine (12 mL), and the solution was subsequently dried over anhydrous MgSO$_4$ and filtered. The solvents were removed in an evaporator and the crude product was purified by column chromatography (Hexane/AcOEt) to obtain the target PAG as a white solid (0.15 g, 14.6% yield). $^1$H-NMR (CDCl$_3$), delta (ppm): 1.23 (s, 9H), 4.65-4.81 (m, 2H), 6.16 (q, J=6.2 Hz, 1H), 7.52-7.63 (m, 2H), 7.68-7.76 (m, 1H), 7.79 (d, J=7.9 Hz, 2H). $^{19}$F-NMR (CDCl$_3$, standard: C$_6$F$_6$=−162.2 ppm), delta (ppm): −72.01 (d, J=6.2 Hz, 3F), −106.73 (dt, J=245.4, 12.8 Hz, 1F), −107.25 (dt, J=245.4, 12.8 Hz, 1F)

Example 12. Preparation of PAG-3

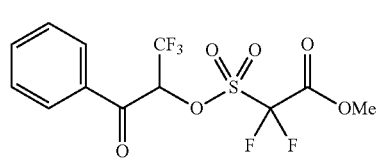

PAG-3

A 50 mL flask was charged with 2-hydroxy-2-trifluoromethylacetophenone (SM-9, 0.98 g, 4.80 mmol, 1.0 eq.) and THF (12 mL) under nitrogen stream and the mixture was stirred for 10 minutes at −30° C. nBuLi (1.6 M, 1.5 mL, 2.40 mmol, 1.0 eq.) was added drop-wise to the mixture over 10 minutes and the mixture was stirred for 30 minutes at −20° C. This solution was then added to a cold (−20° C.) solution of methyl 2,2-difluoro-2-(fluorosulfonyl)acetate (Sigma-Aldrich, 0.92 g, 4.80 mmol, 1.0 eq.) in THF (12 mL) over 5 minutes and the mixture was stirred for 2.5 hours while warming from −20° C. to 20° C. 1N HCl (24 mL) was added to the final reaction mixture and then Et$_2$O (72 mL) was added. The upper layer was separated and washed with 1N HCl (24 mL), the lower layer was extracted with Et$_2$O (48 mL), and the organic layers were combined. This solution was washed with brine (24 mL) twice and was subsequently dried over anhydrous MgSO$_4$ and filtered. Solvents were removed in an evaporator and the crude product was purified by column chromatography (hexane/AcOEt) to obtain the target PAG as a colorless oil (0.02 g, 1.3% yield). $^1$H-NMR (CDCl$_3$), delta (ppm): 4.01 (s, 3H), 6.20 (q, J=6.2 Hz, 1H), 7.58 (t, J=7.9 Hz, 2H), 7.71-7.77 (m, 1H), 7.99 (d, J=7.4 Hz, 2H). $^{19}$F-NMR (CDCl$_3$, standard: C$_6$F$_6$=−162.2 ppm), delta (ppm): −71.98 (d, J=6.2 Hz, 3F), −104.57 (d, J=249.0 Hz, 1F), −105.09 (d, J=249.0 Hz, 1F).

Example 13. Preparation of PAG-4

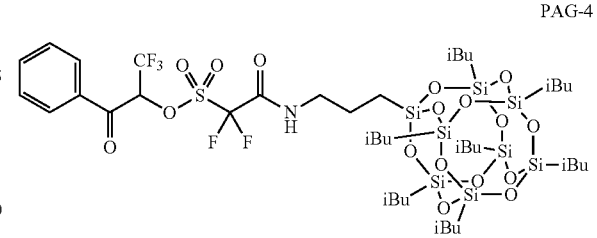

PAG-4

50 mL flask was charged with 2-hydroxy-2-trifluoromethylacetophenone (SM-9, 0.49 g, 2.40 mmol, 1.0 eq.) and THF (6 mL) under nitrogen stream and the mixture was stirred for 10 minutes at −30° C. n-BuLi (1.6 M, 1.5 mL, 2.40 mmol, 1.0 eq.) was added drop-wise to the mixture over 10 minutes and the mixture was stirred for 30 minutes at −30° C. This solution was added drop-wise to a cold (−30° C.) solution of 1,1-difluoro-2-oxo-2-(3-(heptaisobutyl-POSS)propylamino)ethane-1-sulfonyl fluoride (SM-4, 2.10 g, 2.40 mmol, 1.0 eq.) in THF (6 mL) over 5 minutes and the mixture was stirred for 3 hours while warming from −30° C. to 10° C. 1N HCl (12 mL) was added to the final reaction mixture and then AcOEt (36 mL). The upper layer was separated and washed with 1N HCl (12 mL), the lower layer was extracted with AcOEt (24 mL), and then organic layers were combined. This solution was washed with brine (12 mL) twice and the solution was subsequently dried over anhydrous MgSO₄ and filtered. Solvents were removed in an evaporator and the crude product was purified by column chromatography (hexane/AcOEt) to obtain the target PAG as a white solid (0.65 g, 25.6% yield). ¹H-NMR (CDCl₃), delta (ppm): 0.62 (d, J=7.0 Hz, 16H), 0.96 (dd, J=6.6, 4.6 Hz, 42 Hz), 1.68-1.76 (m, 2H), 1.86 (dq, J=13.4, 6.7 Hz, 7H), 3.40 (dp, J=19.9, 6.4 Hz, 2H), 6.38 (q, J=6.2 Hz, 1H), 6.91 (s, 1H), 7.55-7.62 (m, 2H), 7.71-7.77 (m, 1H), 7.96-8.03 (m, 2H). ¹⁹F-NMR (CDCl₃, standard: C₆F₆=−162.2 ppm), delta (ppm): −71.93 (d, J=6.2 Hz, 3F), −105.57 (d, J=245.1 Hz, 1F), −107.04 (d, J=245.1 Hz, 1F).

Example 14. Preparation of PAG-5

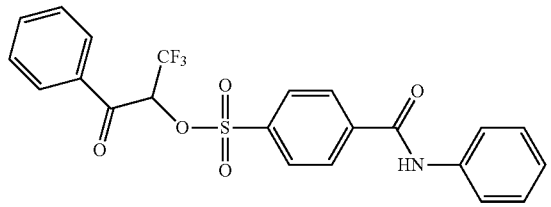

PAG-5

To a 100 mL round bottom flask 4-(phenylcarbamoyl)benzenesulfonyl chloride (SM-5, 2.08 g, 7 mmol), 2-hydroxy-2-trifluoromethylacetophenone (SM-9, 0.89 g, 5 mmol), DCM (20 mL), THF (10 mL), and TEA (0.7 mL) were added. The reaction was then purged with nitrogen and reacted at room temperature for a period of 18 hours. After the reaction the solution was further diluted with DCM (~100 mL), extracted two times with 1M HCl, and dried over anhydrous MgSO₄. The crude product was recrystallized from a minimum amount of CHCl₃ and excess MeOH to give the analytically pure PAG-5. ¹H NMR (400 MHz, DMSO-d₆), delta (ppm): 10.57 (s, 1H), 8.45-8.12 (m, 9H), 7.86-7.73 (m, 4H), 7.70-7.56 (m, 3H), 7.39 (t, J=7.9 Hz, 3H), 7.25 (t, J=6.4 Hz, 2H), 7.21-7.08 (m, 2H). ¹⁹F NMR (376 MHz, DMSO), delta (ppm): −70.93, −70.95.

Example 15. Preparation of PAG-6

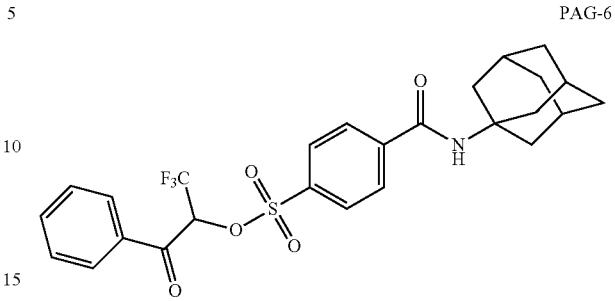

PAG-6

4-((adamantan-1-yl)carbamoyl)benzenesulfonyl chloride (SM-6, 0.933 g, 2.637 mmol) was added to a 100 mL round bottom flask along with 2-hydroxy-2-trifluoromethylacetophenone (SM-9, 0.538 g, 2.64 mmol), DCM (10 mL), and TEA (0.370 mL, 1 eq.). The reaction was then purged with nitrogen and magnetically stirred at room temperature for a period of 18 hours. The solution was further diluted with DCM (~100 mL) and extracted twice with 0.5 M HCl and dried over anhydrous MgSO₄. The crude product was recrystallized from toluene to give the analytically pure PAG-6. ¹H NMR (400 MHz, Chloroform-d), delta (ppm): 8.02-7.88 (m, 3H), 7.83 (d, J=8.5 Hz, 1H), 7.74-7.64 (m, 1H), 7.53 (t, J=7.9 Hz, 2H), 6.02 (q, J=6.4 Hz, 1H), 5.81 (s, 1H), 2.23-2.06 (m, 9H), 1.75 (t, J=2.9 Hz, 7H). ¹⁹F NMR (376 MHz, CDCl₃), delta (ppm): −71.45, −71.46.

Example 16. Preparation of DPAG-1

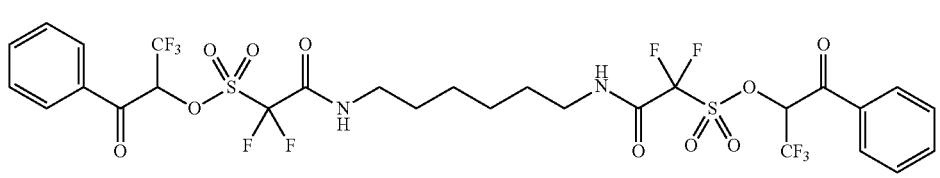

DPAG-1

A 50 mL flask was charged with 2-hydroxy-2-trifluoromethylacetophenone (SM-9, 0.60 g, 2.93 mmol, 2.0 eq.) and THF (7.5 mL) under nitrogen stream and the mixture was stirred for 10 minutes at −30° C. n-BuLi (1.6 M, 1.8 mL, 2.93 mmol, 2.0 eq.) drop-wise to the mixture over 10 minutes and the mixture was stirred for 30 minutes at −30° C. This solution was added drop-wise to a cold (−30° C.) solution of 2,2'-(hexane-1,6-diylbis(azanediyl)bis(1,1-difluoro-2-oxoethane-1-sulfonyl fluoride) (SM-7, 0.64 g, 1.47 mmol, 1.0 eq.) in THF (7.5 mL) over 5 minutes and the mixture was stirred for 4 hours while warming from −30° C.

to 10° C. 1N HCl (15 mL) was added to the final reaction mixture and then Et$_2$O (45 mL) was added. The upper layer was separated and washed with 1N HCl (15 mL) and the lower layer was extracted with Et$_2$O (30 mL). The organic layers were combined and washed with brine (15 mL) twice and was subsequently dried over anhydrous MgSO$_4$ and filtered. Solvents were removed in an evaporator and CHCl$_3$ (100 mL) was added to the crude material. An insoluble solid was filtrated off and the filtrate was washed with saturated aqueous NaHCO$_3$ (5×15 mL). The lower layer was separated and concentrated in an evaporator. The target PAG was obtained as a colorless oil (0.09 g, 4.9% yield). $^1$H-NMR (CDCl$_3$), delta (ppm): 1.40 (t, J=6.5 Hz, 4H), 1.63 (t, J=6.8 Hz, 4H), 3.32-3.50 (m, 4H), 6.38 (q, J=6.2 Hz, 2H), 7.59 (t, J=7.8 Hz, 4H), 7.75 (t, J=7.4 Hz, 2H), 7.99 (d, J=7.7 Hz, 4H). $^{19}$F-NMR (CDCl$_3$, standard: C$_6$F$_6$=−162.2 ppm), delta (ppm): −71.95 (d, J=6.2 Hz, 6F), −105.74 (d, J=244.0 Hz, 2F), −107.53 (d, J=244.5 Hz, 2F)

Example 17. Preparation of DPAG-2

DPAG-2

50 mL flask was charged with 2-hydroxy-2-trifluoromethylacetophenone (SM-9) (0.98 g, 4.80 mmol, 2.0 eq.) and THF (12 mL) under nitrogen stream and the mixture was stirred for 10 minutes at −30° C. n-BuLi (1.6 M, 3.0 mL, 4.80 mmol, 2.0 eq.) was added drop-wise to the mixture over 10 minutes and the mixture was stirred for 30 minutes at −30° C. This solution was added to a cold (−30° C.) solution of 2,2'-(1,3-phenylenebis(azanediyl))bis(1,1-difluoro-2-oxoethane-1-sulfonyl fluoride) (SM-8, 1.03 g, 2.40 mmol, 1.0 eq.) in THF (12 mL) over 5 minutes and the mixture was then stirred for 3 hours at −30 to 10° C. 1N HCl (24 mL) was added to the final reaction mixture and then Et$_2$O (72 mL) was added. The upper layer was separated and washed with 1N HCl (24 mL) and the lower layer was extracted with Et$_2$O (48 mL) and then the organic layers were combined. This solution was washed with brine (24 mL) twice and was subsequently dried over anhydrous MgSO$_4$ and filtered. Solvents were removed in an evaporator and then CHCl$_3$ (100 mL) was added to the residue. An insoluble solid was filtrated off and the filtrate was washed with saturated aqueous NaHCO$_3$ (20 mL) four times and then the lower layer was separated and concentrated in the evaporator. The crude product was purified by column chromatography (Hexane/CH$_2$Cl$_2$) and (Hexane/AcOEt) to obtain the target PAG as white solid (0.09 g) in 4.9% yield. $^1$H-NMR (CDCl$_3$), delta (ppm): 6.41-6.49 (m, 2H), 7.47 (t, J=8.2 Hz, 1H), 7.62 (dt, J=15.7, 8.0 Hz, 6H), 7.78 (t, J=6.9 Hz, 2H), 8.02 (d, J=8.1 Hz, 4H), 8.16 (d, J=6.5 Hz, 1H), 9.16 (d, J=5.6 Hz, 2H). $^{19}$F-NMR (CDCl$_3$, standard: C$_6$F$_6$=−162.2 ppm), delta (ppm): −71.73 (d, J=6.2 Hz, 6F), −104.94 (dd, J=245.0, 15.2 Hz, 2F), −108.93 (dd, J=244.5, 12.8 Hz, 2F)

Example 18. Preparation of Comparative PAG, CPAG-1, Adapted from the Procedure of JP2002236358A

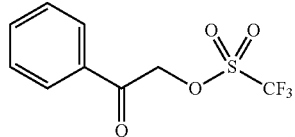

CPAG-1

A 100 mL flask was charged with (diacetoxyiodo)benzene (3.22 g, 10.0 mmol, 1.0 eq.) and CH$_3$CN (25 mL) under nitrogen stream and the mixture was stirred for 5 minutes at room temperature. The CH$_3$CN (25 mL) solution of trifluoromethanesulfonic acid (3.00 g, 20.0 mmol, 2.0 eq.) and H$_2$O (0.36 g, 20.0 mmol, 2.0 eq.) was added drop-wise to the mixture over 5 minutes and the mixture was stirred for 10 minutes at room temperature. Acetophenone (1.20 g, 10.0 mmol, 1.0 eq.) was added to the mixture and the mixture was stirred for 2.5 hours at room temperature. The mixture was then concentrated in an evaporator. The residue was extracted with hexane (50 mL) twice and the hexane layers were combined followed by removing the hexane in an evaporator. The crude product was purified by recrystallization (hexane, 35° C. to 0° C.) to obtain the target compound as a white solid (0.113 g, 4.2% yield). $^1$H-NMR (CDCl$_3$), delta (ppm): 5.68 (s, 2H), 7.57 (dd, J=8.0, 7.4 Hz, 2H), 7.71 (tt, J=1.2, 7.5 Hz, 1H), 7.92 (dd, J=1.3, 7.9 Hz, 2H). $^{19}$F-NMR (CDCl$_3$, standard: C$_6$F$_6$=−162.2 ppm), delta (ppm): −75.13 (s, 3F).

Example 19. Preparation of Comparative PAG, CPAG-2

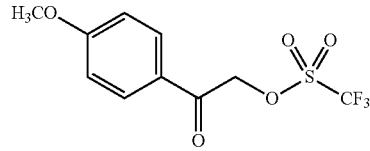

CPAG-2

A 100 mL flask was charged with (diacetoxyiodo)benzene (3.22 g, 10.0 mmol, 1.0 eq.) and CH$_3$CN (25 mL) under nitrogen stream and the mixture was stirred for 5 minutes at room temperature. The CH$_3$CN (25 mL) solution of trifluoromethanesulfonic acid (3.00 g, 20.0 mmol, 2.0 eq.) and H₂O (0.36 g, 20.0 mmol, 2.0 eq.) was added drop-wise to the mixture over 5 minutes and the mixture was stirred for 30 minutes at room temperature. 4-Methoxyacetophenone (1.50 g, 10.0 mmol, 1.0 eq.) was added to the mixture and the mixture was stirred for 3.5 hours at room temperature and the mixture was concentrated in an evaporator. The concentrate was extracted with hexane (100 mL) twice and hexane layers were combined followed by removing the hexane in an evaporator. The crude product was purified by recrystallization (hexane/CHCl₃, 50° C. to 0° C.) to obtain the target compound as white solid (0.096 g, 3.2% yield). ¹H-NMR (CDCl₃), delta (ppm): 3.92 (s, 3H), 5.62 (s, 2H), 7.01 (d, J=9.0 Hz, 2H), 7.89 (d, J=9.0 Hz, 2H). ¹⁹F-NMR (CDCl₃, standard: C₆F₆=−162.2 ppm), delta (ppm): −75.27 (s, 3F).

Example 20. Preparation of Comparative PAG, CPAG-3

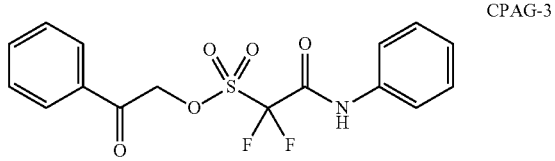 [SMILES: O=C(COS(=O)(=O)C(F)(F)C(=O)Nc1ccccc1)c1ccccc1]

CPAG-3

A 200 mL flask was charged with 1-difluoro-2-oxo-2-(phenylamino)ethane-1-sulfonyl fluoride (SM-1, 2.53 g, 10.0 mmol, 1.0 eq.), 2-hydroxyacetophenone (Sigma-Aldrich) (1.36 g, 10.0 mmol, 1.0 eq.) and THF (50 mL) under nitrogen stream and the mixture was stirred for 10 minutes at −30° C. nBuLi (1.6 M, 6.3 mL, 10.0 mmol, 1.0 eq.) was added drop-wise to the mixture over 10 minutes. The mixture was allowed to warm to 0° C. and stirred for 2 hours at 0° C. 1N HCl (50 mL) was added to the final reaction mixture and then AcOEt (150 mL) was added. The upper layer was separated and washed with saturated aqueous NaHCO₃ (3×25 mL) and brine (15 mL). The solution was subsequently dried over anhydrous MgSO₄ and filtered. Solvents were removed in an evaporator and CH₂Cl₂ (50 mL) was added to the crude material. The sodium salt separated and was removed by filtration. The filtrate was concentrated in an evaporator and the residue was washed with hexane (2×40 mL). The hexane was removed by decantation, and the obtained crude product was purified by recrystallization (hexane/CH₂Cl₂, 40° C. to 0° C.) to obtain the target PAG as a white solid (0.69 g, 18.8% yield). ¹H-NMR (CDCl₃), delta (ppm): 5.86 (s, 2H), 7.27 (t, J=7.4 Hz, 1H), 7.44 (dd, J=8.4, 7.5 Hz, 2H), 7.61 (dd, J=7.7, 7.9 Hz, 2H), 7.76 (dt, J=1.2, 7.5 Hz, 1H), 7.82 (dd, J=1.1, 8.2 Hz, 2H), 7.99 (dd, J=1.2, 8.4 Hz, 2H), 10.00 (brs, 1H). ¹⁹F-NMR (CDCl₃, standard: C₆F₆=−162.2 ppm), delta (ppm): −108.26 (s, 2F).

Example 21. Preparation of Comparative PAG, CPAG-4

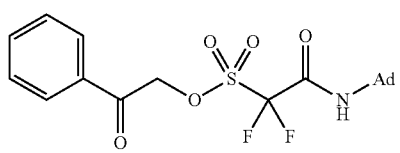

CPAG-4

A 100 ml flask was charged with 1, 1-difluoro-2-oxo-2-(1-adamantylamino)ethanesulfonyl fluoride (SM-2) (1.49 g, 4.80 mmol, 1.0 eq.), 2-hydroxyacetophenone (Sigma-Aldrich) (0.65 g, 4.80 mmol, 1.0 eq.) and THF (24 mL) under nitrogen stream and the mixture was stirred for 5 min at −50° C. nBuLi (1.6 M, 3.0 ml, 4.80 mmol, 1.0 eq.) was added drop-wise to the mixture over 10 minutes. The mixture was stirred for 2 hours while warming from −50° C. to 10° C. 1N HCl (24 ml) was added to the final reaction mixture and then Et₂O (72 mL) was added. The upper layer was separated and the lower layer was extracted with Et₂O (48 ml). The organic solutions were combined and the solvents were removed in an evaporator (25° C.) and the residue was washed with hexane (4×20 mL). The hexane was removed by decantation and the crude product was purified by column chromatography (hexane/AcOEt) to obtain the target PAG as a brown oil (0.42 g, 20.5% yield). ¹H-NMR (CDCl₃), delta (ppm): 1.72 (brs, 6H), 2.14 (brs, 9H), 5.71 (s, 2H), 6.98 (brs, 1H), 7.56 (dd, J=7.8, 7.9 Hz, 2H), 7.70 (tt, J=1.2, 7.5 Hz, 1H), 7.93 (dd, J=1.2, 8.0 Hz, 2H). ¹⁹F-NMR (CDCl₃, standard: C₆F₆=−162.2 ppm), delta (ppm): −107.73 (s, 2F).

Example 22. Preparation of Comparative PAG, CPAG-5

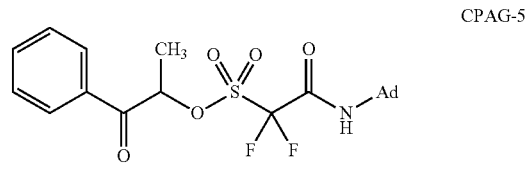

CPAG-5

A 100 mL flask was charged with 1, 1-difluoro-2-oxo-2-(1-adamantylamino)ethanesulfonyl fluoride (SM-2) (1.62 g, 5.19 mmol, 1.0 eq.), 2-hydroxypropiophenone (SM-10) (0.78 g, 5.19 mmol, 1.0 eq.) and THF (26 mL) under nitrogen stream and the mixture was stirred for 5 minutes at −50° C. nBuLi (1.6 M, 3.2 mL, 5.19 mmol, 1.0 eq.) was added drop-wise to the mixture over 10 minutes. The mixture was stirred for 2 hours at −50 to 10° C. 1N HCl (26 mL) was added to the final reaction mixture and then AcOEt (78 mL) was added. The upper layer was separated and the lower layer was extracted with AcOEt (52 mL) and then the organic solutions were combined. This solution was washed with 1N HCl (26 mL) and brine (26 mL) and the solution was subsequently dried over anhydrous MgSO₄ and filtered. Solvents were removed in an evaporator and then hexane (75 mL) was added to the residue and the mixture was stirred for 10 minutes at −50° C. The hexane was then removed by decantation. CHCl₃ (100 mL) was added to the residue and the solid remained was filtrated off. The filtrate was then concentrated in an evaporator. This crude product was partially purified by column chromatography (hexane/AcOEt) to obtain an oily material. Hexane (30 mL) was added to the concentrated oil and the mixture was stirred for 10 minutes at −50° C. Hexane was removed by decantation and CHCl₃ (30 mL) was added to the remaining material and filtrated. Filtrate was concentrated in an evaporator and the target PAG as colorless oil (0.22 g) in 9.6% yield was obtained. ¹H-NMR (CDCl₃), delta (ppm): 1.73 (brs, 6H), 1.79 (d, J=7.0 Hz, 3H), 2.10 (brs, 6H), 2.15 (brs, 3H), 6.18 (q, J=7.1 Hz, 1H), 6.62 (drs, 1H), 7.55 (dd, J=7.4, 8.0 Hz, 2H), 7.68 (tt, J=1.3, 7.4 Hz, 1H), 7.95 (dd, J=1.3, 8.4 Hz, 2H), $^{19}$F-NMR (CDCl$_3$, standard: C$_6$F$_6$=−162.2 ppm), delta in ppm: −106.89 (d, J=242.10, 1F), −109.19 (d, J=241.8 Hz, 1F).

Example 23. Attempted Preparation of Comparative PAG, CPAG-6

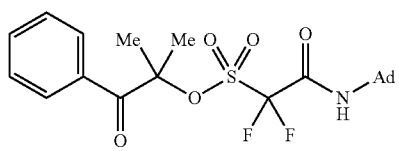
CPAG-6

In an attempt to synthesize the above compound starting with 1,1-difluoro-2-oxo-2-(1-adamantylamino)ethanesulfonyl fluoride (SM-2) and 2-hydroxy-2-methylpropiophenone (Sigma-Aldrich), using a procedure similar to the one described in the synthesis of CPAG-5 (reaction scheme below), no product was isolated.

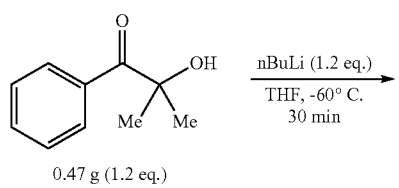

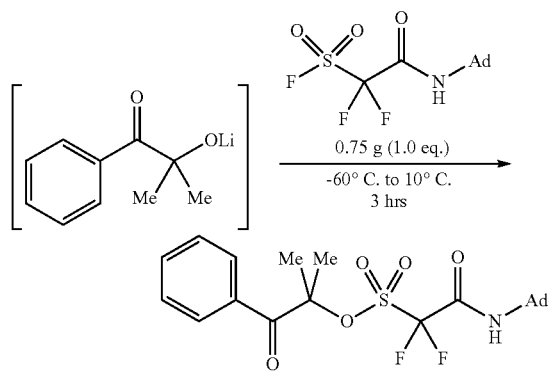

The conversion of target compound was low and the target compound seemed to have decomposed during the reaction and treatment. Peaks derived from difluoromethylsulfonic acid (decomposition product) were confirmed after treatment ($^{19}$F NMR: −100.2 and −108.70 ppm). The target PAG was not isolable even when the reaction condition were changed.

PAG Thermal Stability

Table 2 summarizes the thermogravimetric analysis (TGA) data and differential scanning calorimetry (DSC) data for some of the PAG compounds. $T_d$ TGA (° C.) is the main decomposition temperature according to TGA. Mp DSC (° C.) is the melting point. $T_d$ DSC (° C.) is the main decomposition temperature according to DSC.

TABLE 2

| Example | Name | $T_d$ TGA (° C.) | Mp DSC (° C.) | $T_d$ DSC (° C.) |
|---|---|---|---|---|
| 10 | PAG-1 | 205 | 74.11 | 195 |
| 11 | PAG-2 | | | |
| 12 | PAG-3 | | | |
| 13 | PAG-4 | | | |
| 14 | PAG-5 | 250 | 153.7 | — |
| 15 | PAG-6 | 224 | 163.7 | — |
| 16 | DPAG-1 | | | |
| 17 | DPAG-2 | | | |
| 18 (comp) | CPAG-1 | 85 | 54.6 | 120 |
| 19 (comp) | CPAG-2 | 115 | 75.0 | — |
| 20 (comp) | CPAG-3 | 155 | 109.7 | 140 |
| 21 (comp) | CPAG-4 | 111 | 101.0 | 105 |
| 22 (comp) | CPAG-5 | 89 | 122.6 | 90 |
| 23 (comp) | CPAG-6 | not isolated | not isolated | not isolated |

Figure 3:
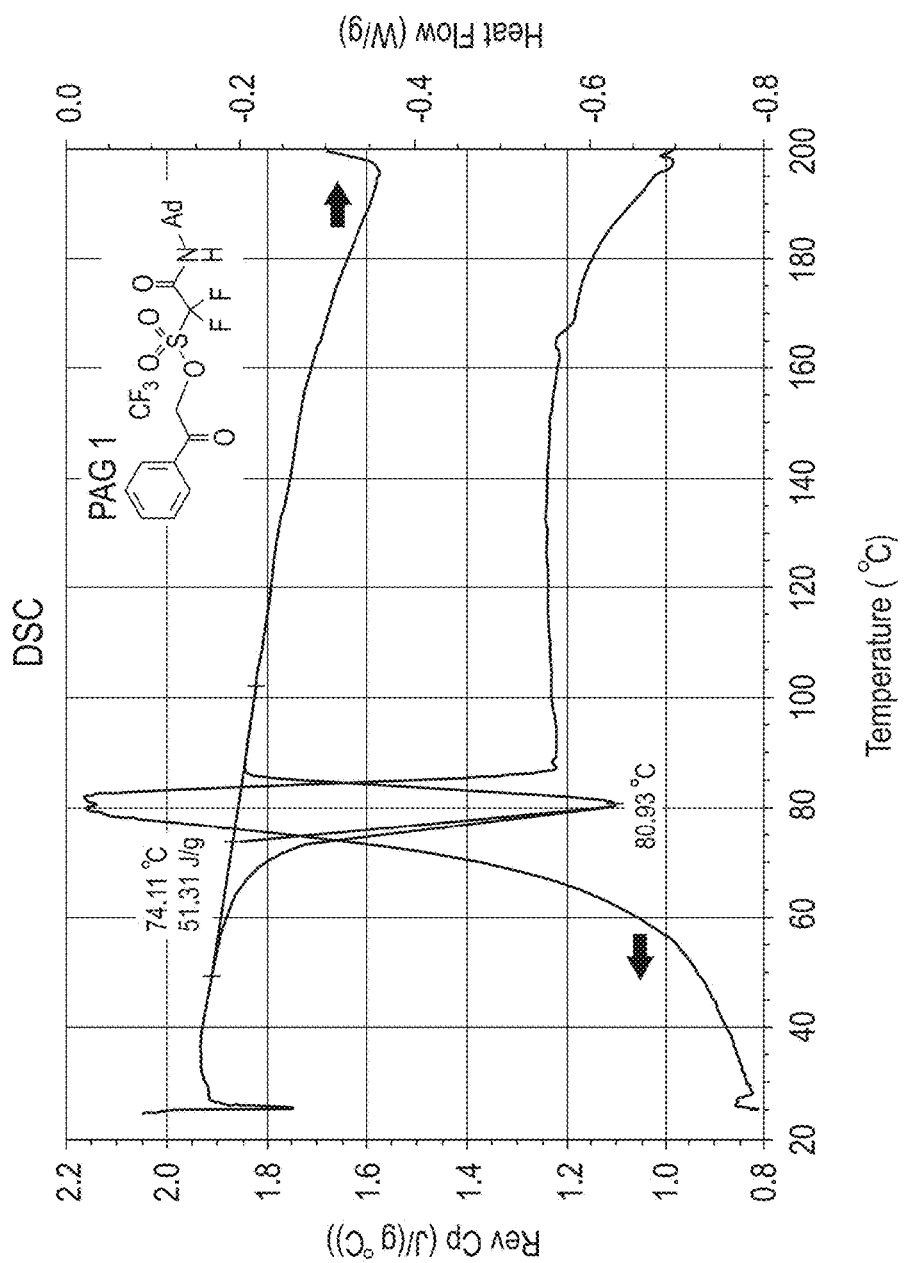
FIG. 3 is a graph of the differential scanning calorimetry (DSC) curves for PAG-1 (Example 10).
Figure 6A:
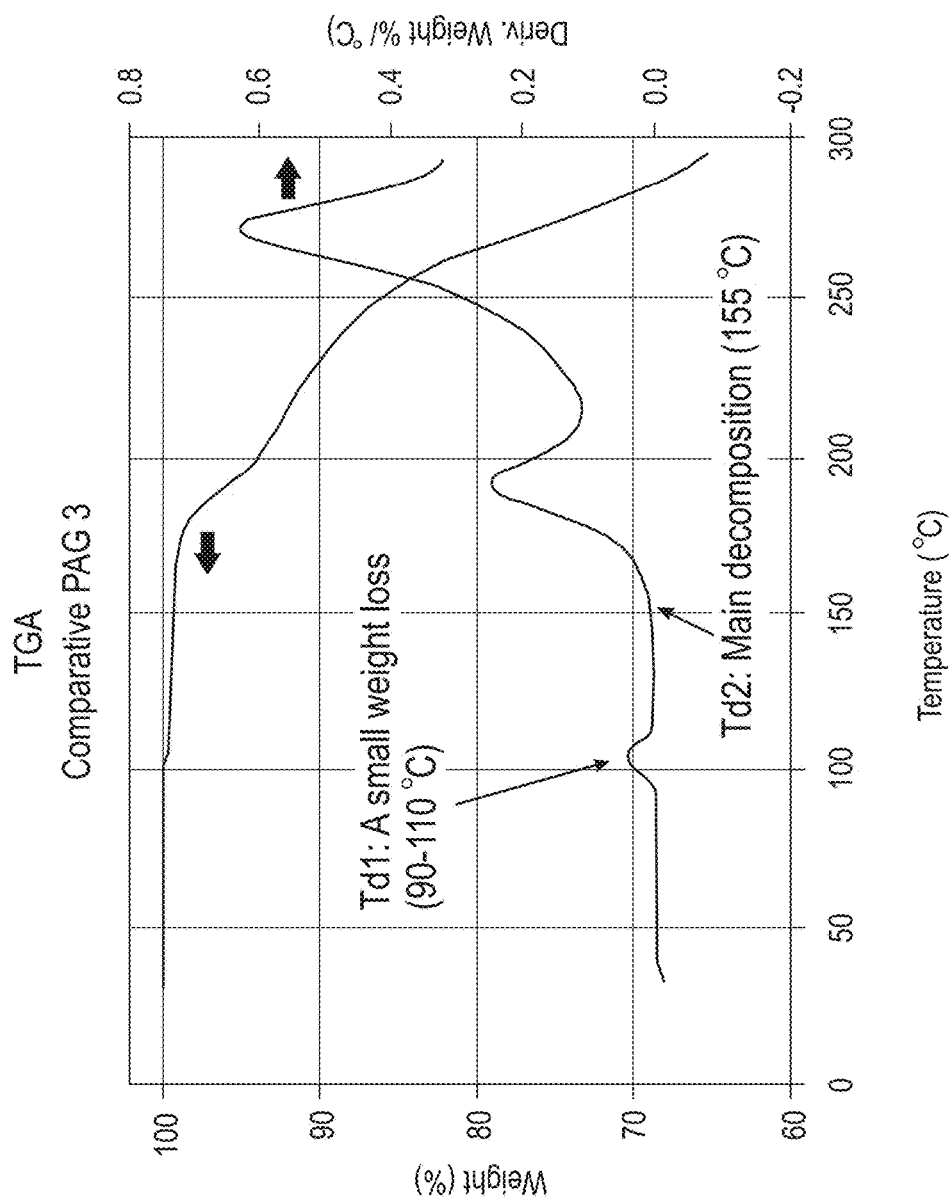
FIG. 6A is a graph showing the TGA curves for CPAG-3 (comparative Example 20).
Figure 6B:
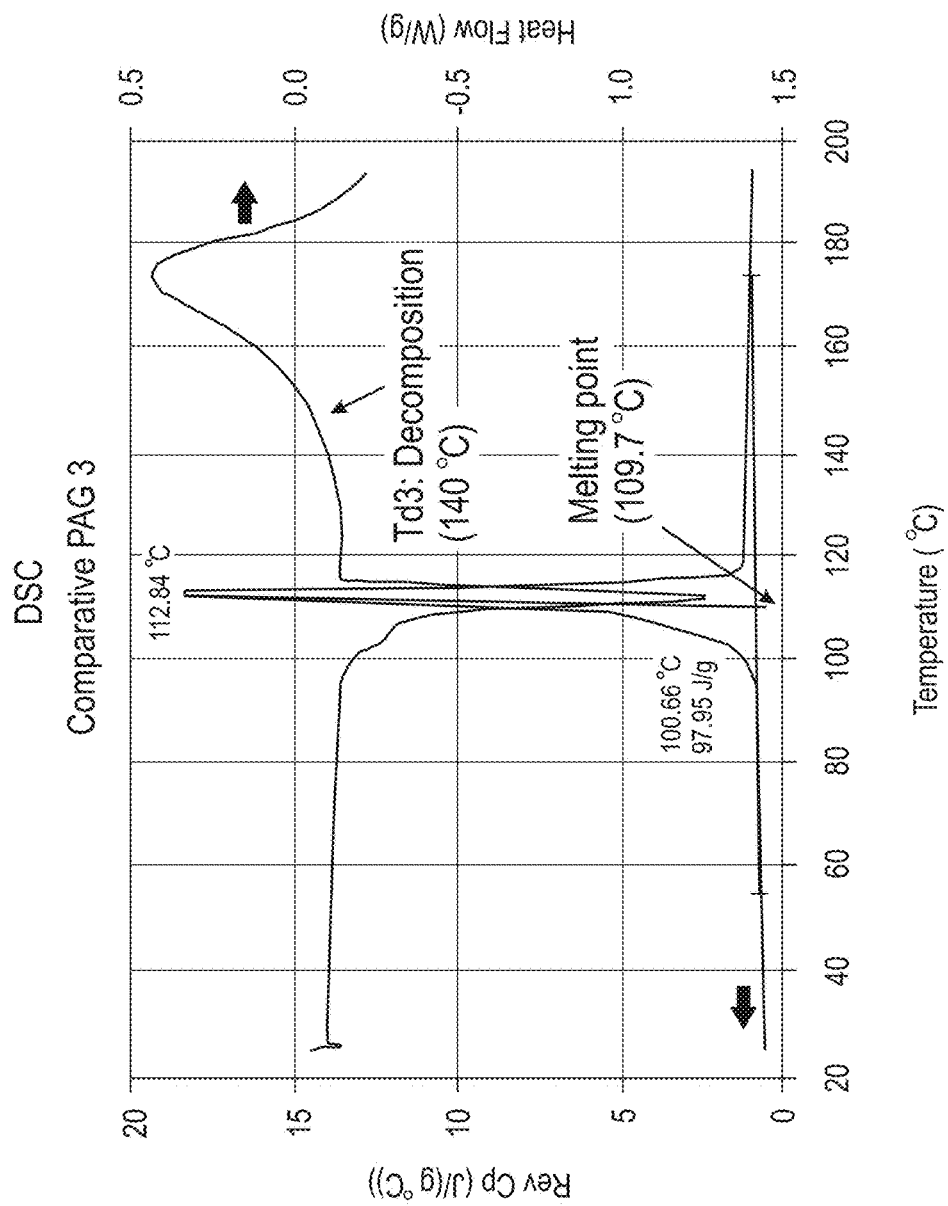
FIG. 6B is a graph showing the DSC curves for CPAG-3 (comparative Example 20).
Figure 7:
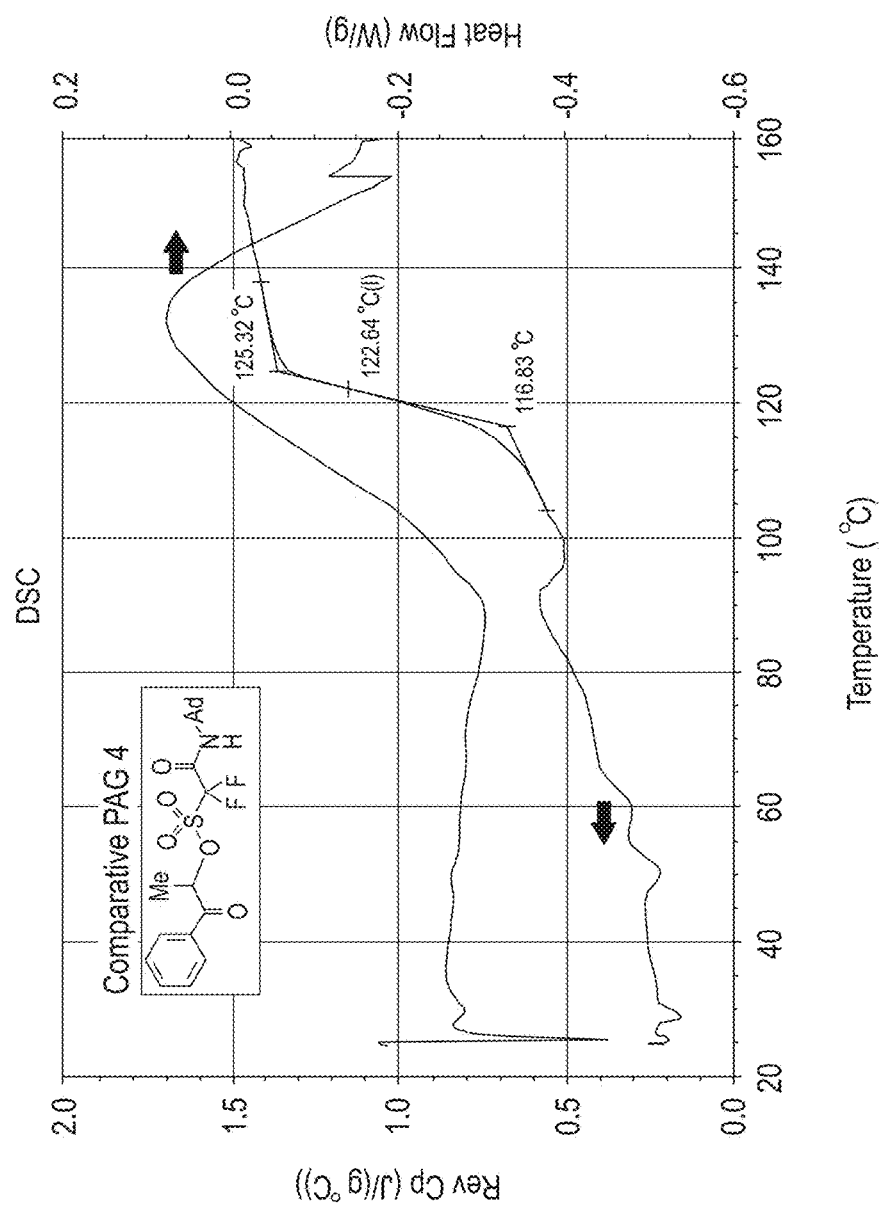
FIG. 7 is a graph showing the DSC curves for CPAG-4 (comparative Example 21, comparative).
Figure 8:
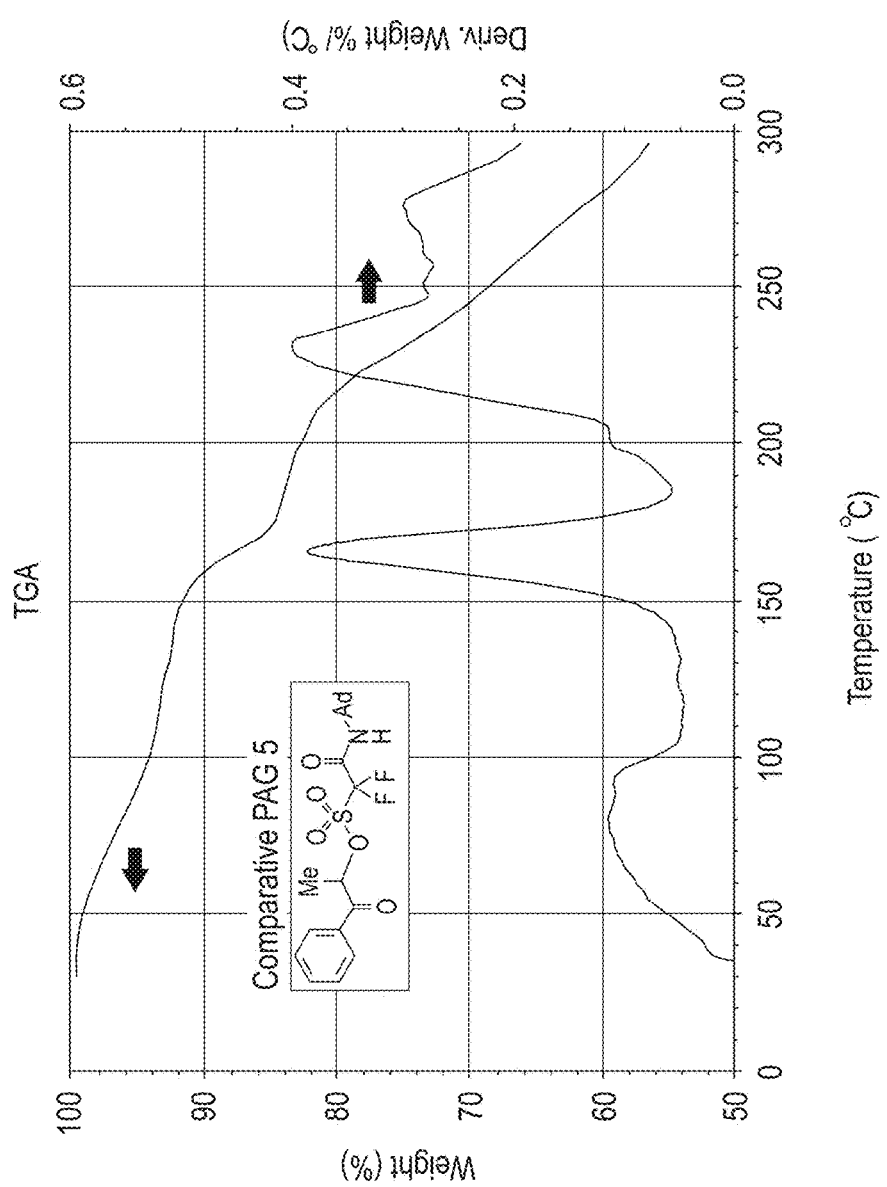
FIG. 8 is a graph showing the DSC curves for CPAG-5 (comparative Example 22, comparative).

Examples 10-17 of Table 2 were relatively thermally stable whereas the comparative PAG compounds were not. For example, PAG-1 has a decomposition temperature of about 195° C. (FIG. 3, DSC), whereas the comparative PAGS had the following decomposition temperatures: CPAG-1 decomposed at 85° C. by TGA (FIG. 4), CPAG-2 decomposed at 115° C. by TGA (FIG. 5), CPAG-3 decomposed at 155° C. by TGA (FIG. 6A) and at 140° C. by DSC (FIG. 6B), CPAG-4 decomposed at 105° C. by DSC (FIG. 7, DSC), and CPAG-5 decomposed at 90° C. by DSC (FIG. 8, DSC). Despite the comparatively higher thermal stability of CPAG-3 relative to the other comparative PAG compounds, the positive resist formulation with this PAG was unstable. The inventive PAGs having the α-CF$_3$ group exhibit increased hydrolytic stability and thermal stability relative to the comparative PAGs having only hydrogens at the alpha position to the carbonyl. Without being bound by theory, the improved hydrolytic stability may be due to the increase in steric hindrance reducing nucleophilic attack by water or other nucleophiles. The greater hydrolytic (and nucleophilic) stability affords greater stability in solution, in formulated photoresists, and/or in photoresist coatings by avoiding the deleterious production of acid by mechanisms other than exposure to radiation.

Polymer Synthesis

A standard acid-labile polymer, P(NBHFAMA-co-ECPMA) 60:40 m/m, was used as the base polymer in the formulations for the evaluation of the PAGs. End groups are not shown in the structure below.

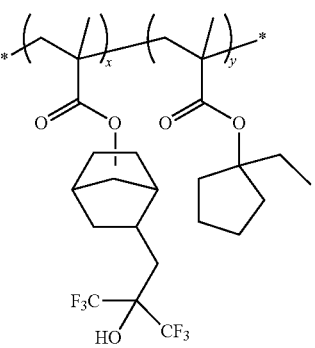

P(NBHFAMA-co-ECPMA)
x:y = 60:40 mol %

Example 24 Preparation of Acid-Labile Polymer P-1

NBHFAMA (10.80 grams, 0.03 mole), ECPMA (3.64 grams, 0.02 mole), and 58 grams of tetrahydrofuran (THF) were placed in a round bottom flask equipped with a condenser and a nitrogen inlet. To this solution, 2,2'-azobisisobutyronitrile (AIBN) (0.33 gram, 0.002 mole) and 1-dodecanethiol (0.30 gram, 0.0015 mole) were added and stirred until dissolved. Then, the solution was degassed using four vacuum/nitrogen purges. The solution was then heated at 70° C. in an oil bath for 18 hours. Afterwards, the solution was added drop-wise into hexanes (1.2 liter). The precipitated polymer was filtered through a medium frit funnel, washed with 100 mL hexanes, and dried under suction. The polymer was then dried in a vacuum oven at 60° C. Yield: 5.06 grams; Mw 11890; Mn 9355; polydispersity (PDI): 1.27; Tg: 150.8° C.

Resist Formulations

Resist compositions were prepared by forming a 3.5 wt % (weight %) solution, based on total weight of the solution, in propylene glycol monomethyl ether acetate (PGMEA) containing 100 parts polymer P(NBHFAMA-co-ECPMA) 60:40, 4 to 5 parts of PAG, and 0.33 or 0.66 parts of an organic base, 2-phenyl benzimidazole (quencher 1). The solution was then filtered through 0.2 micrometer PTFE syringe filter. The formulations were not optimized.

Examples 10-17 were stable in the resist formulation. Comparative PAG CPAG-5 (Example 22) was not stable in resist formulation. For example, the resist formulation with CPAG-5 decomposed within one week, indicating that an alkyl or aryl group substituent at the alpha-position of the aryl ketone group makes the PAG less stable. In theory, substituent groups such as methyl at the alpha position to the carbonyl can stabilize the partial positive charge that is develops on the alpha carbon during thermal elimination of the sulfonate group. This facilitates the elimination reaction at lower temperatures. Similarly, CPAG-6 with two electron-donating methyl groups at the alpha-position is so unstable it cannot be isolated. This is in agreement with the general stability of carbocations (tertiary>secondary>primary). In contrast, the inventive PAGs (e.g., Examples 10-17) have an electron-withdrawing substituent in the alpha position which inductively destabilizes the formation of any partial positive charge on the alpha carbon, thereby disfavoring elimination and increasing the thermal stability of the PAG.

Line Patterns

The resist formulation was spin coated to a thickness between 30 to 50 nm onto silicon wafers having a bottom anti-reflective coating (BARC). The BARC underlayer was used for adhesion purposes. The wafer was given a post-apply bake at 110° C. for 60 seconds on a hot plate. The wafer was then exposed on a 0.3-NA extreme ultraviolet (EUV) micro exposure tool (MET) at variable doses. The exposed wafer was given a post-exposure bake at 110° C. for 60 seconds. Both bakes were done with the wafer in contact with the hot plate. A 60-second development of the resist was carried out using a gentle spray of 0.26 N aqueous tetramethylammonium hydroxide solution (TMAH) to puddle followed by water rinse and spin dry. Top and cross-sectional images were inspected using a LEO Carl Zeiss scanning electron micrograph (SEM) tool. Cross sectional samples were coated with thin PdAu to avoid sample charging.

Results

FIG. 9 is a set of SEM images comparing line patterns formed with CPAG-4 and CPAG-5 when exposed at 13.5 nm using the EUV-MET. CPAG-4 showed lifting and scum at half-pitches 32 nm and 36 nm. No line pattern was obtained with CPAG-5 due to decomposition. The resist formulation contained 1 part PAG and 0.33 parts quencher 1. The dose was 25.24 mJ and the film thickness 40 nm.

Figure 10:
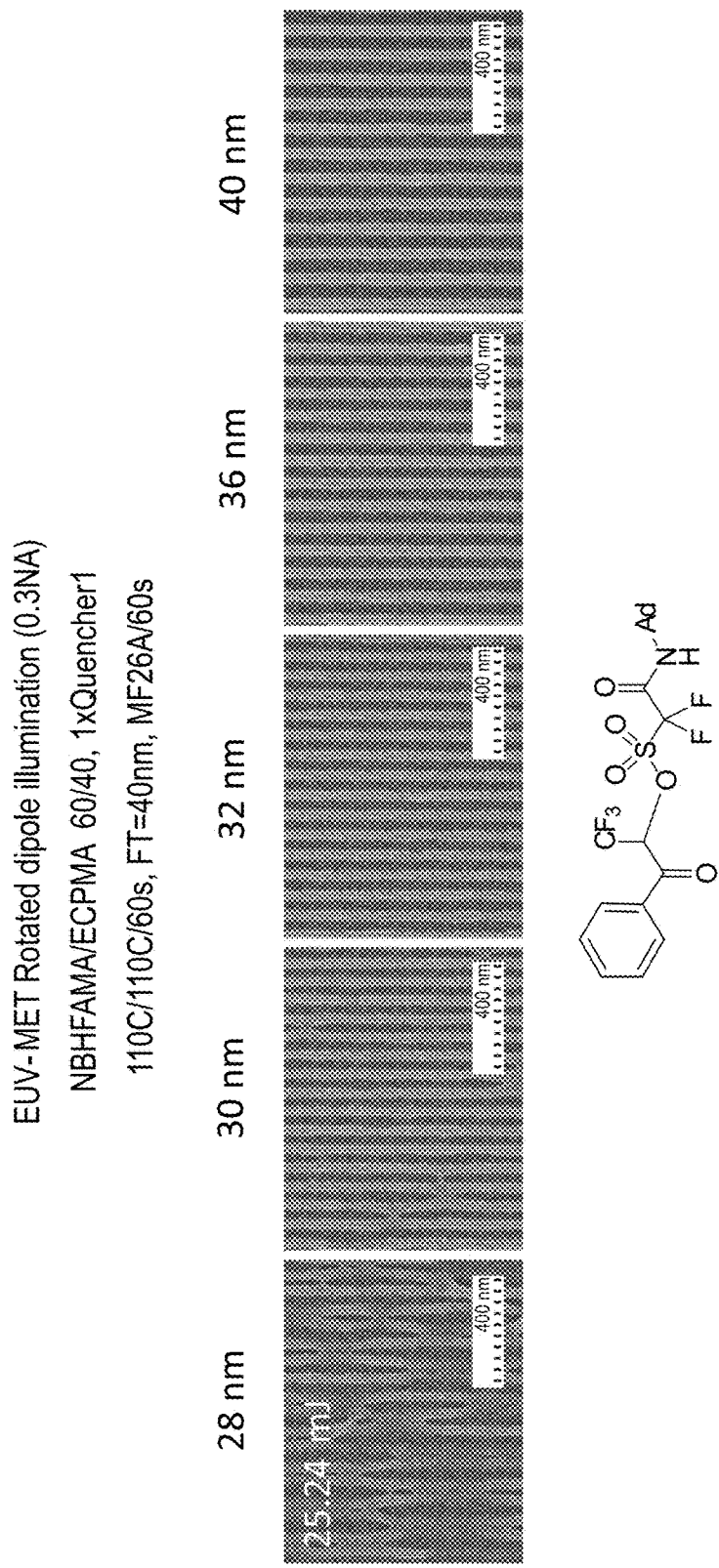
FIG. 10 is a set of SEM images showing line patterns prepared with PAG-1 when exposed at 13.5 nm using EUV-MET.

FIG. 10 is a set of SEM images of line patterns prepared with PAG-1 at half pitches of 28 nm to 40 nm when exposed at 13.5 nm using the EUV-MET. Cleaner line patterns were obtained at each half-pitch compared to FIG. 9. The resist formulation contained 1 part PAG-1 and 0.33 parts quencher 1. The dose was 25.24 mJ and the film thickness was 40 nm.

FIG. 11 is a set of SEM images showing the line patterns formed with PAG-4 when exposed using the EUV-MET.

FIG. 12 is a set of SEM images showing the line patterns formed with PAG-6 when exposed using the EUV-MET.

FIG. 13 is a set of SEM images showing the line patterns formed with DPAG-1 when exposed using the EUV-MET.

The results indicate that PAGs comprising a perfluorinated hydrocarbon substituent on the sulfonate ester methylene exhibit improved thermal stability compared to an otherwise identical PAG compound comprising a non-substituted methylene group or a non-fluorinated hydrocarbon substituent. The results also indicate that PAGs comprising a perfluorinated hydrocarbon substituent on the sulfonate ester methylene exhibit improved hydrolytic/nucleophilic stability compared to an otherwise identical PAG compound comprising a non-substituted methylene group.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without depart-

What is claimed is:

1. A compound of formula (3):

$$\left[ Ar\underset{}{\overset{O}{-}}\overset{R^1}{\underset{}{C}}H-O-\underset{\underset{O}{\|}}{\overset{\overset{O}{\|}}{S}}-L'\right]_n R^2,$$ (3)

wherein
n is a positive integer having a value of 1-4,
Ar is a monovalent aryl radical comprising one or more aromatic rings,
L' is a single bond or a divalent $C_1$-$C_{10}$ linking group,
$R^1$ is a monovalent perfluorinated $C_1$-$C_{10}$ radical, wherein $R^1$ has a molecular formula consisting of elements carbon and fluorine, and
$R^2$ is a $C_1$-$C_{50}$ radical having a valency of n.

2. The compound of claim 1, wherein Ar is selected from the group consisting of

[structures shown]

3. The compound of claim 1, wherein n is 1.

4. The compound of claim 1, wherein $R^1$ is selected from the group consisting of trifluoromethyl (*—$CF_3$), perfluoroethyl (*—$CF_2CF_3$), perfluoro-n-propyl (*—$CF_2CF_2CF_3$), and perfluoro-n-butyl (*—$CF_2CF_2CF_2CF_3$).

5. The compound of claim 1, wherein L' is selected from the group consisting of
i)

[structure shown]

wherein nitrogen 3 is linked to $R^2$,
ii)

[structure shown]

wherein oxygen 3 is linked to $R^2$,
iii)

[structure shown]

wherein oxygen 3 is linked to $R^2$, and
iv)

[structure shown]

wherein nitrogen 3 is linked to $R^2$, and wherein carbon 1 of each of the foregoing groups is linked to the sulfur of formula (3).

6. The compound of claim 1, wherein $R^2$ comprises an adamantyl group.

7. The compound of claim 1, wherein $R^2$ comprises a silsesquioxane group of formula (5):

[structure shown] (5)

wherein
L″ is a divalent $C_1$-$C_6$ linking group, and
Z is a $C_1$-$C_6$ alkyl group.

8. The compound of claim 7, wherein the Z is isobutyl.

9. The compound of claim 1, wherein the compound is selected from the group consisting of (PAG-1)

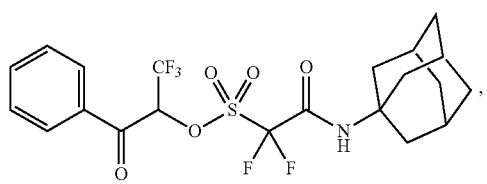

(PAG-2)

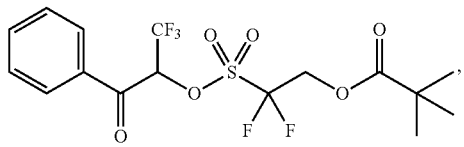

(PAG-3)

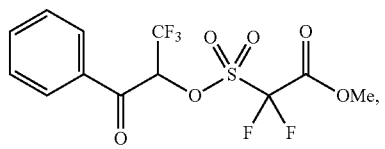

(PAG-4)

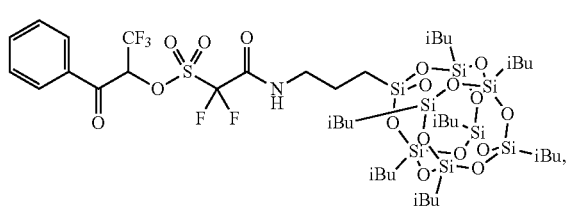

(PAG-5)

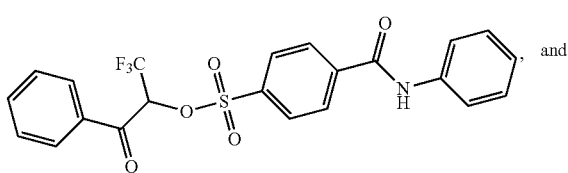
and (PAG-6)

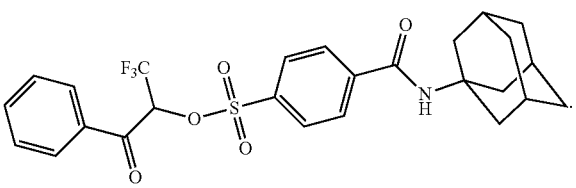

10. The compound of claim 1, wherein n is 2.

11. The compound of claim 10, wherein $R^2$ is 1,3-phenylene.

12. The compound of claim 10, wherein $R^2$ is hexan-1,6-diyl (*—$CH_2(CH_2)_4CH_2$—*).

13. The compound of claim 10, wherein the compound is selected from the group consisting of:

(DPAG-1)

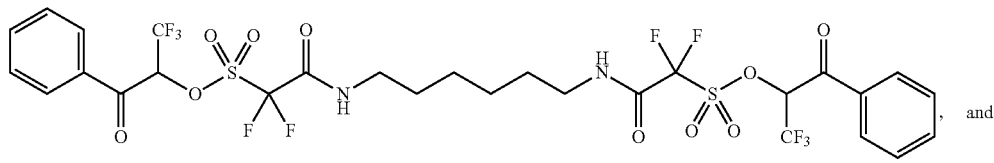
, and (DPAG-2)

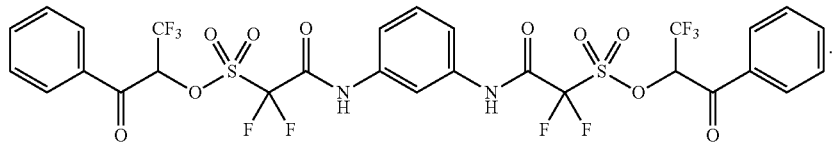

14. A resist formulation, comprising:
a solvent;
a resin capable of chemical amplification;
a base quencher; and
the compound of claim 1;
wherein
the resin, the base quencher, and the compound are in contact with the solvent, and
the resist formulation is suitable for use in a lithographic process.

15. The resist formulation of claim 14, wherein the resist formulation is positive-tone.

16. The resist formulation of claim 14, wherein the resist formulation is negative-tone.

17. The resist formulation of claim 14, wherein the compound is capable of forming an acid when exposed to radiation.

18. The resist formulation of claim 17, wherein the radiation is selected from the group consisting of electron beam, deep ultraviolet light, and extreme ultraviolet light.

19. The resist formulation of claim 14, wherein the compound is capable of forming an acid when heated to a temperature of about 150° C. or higher.

20. A method, comprising:
casting a resist formulation comprising a solvent, a resin capable of chemical amplification, a base, and the compound of claim 1 on a surface of a substrate and removing the solvent, thereby forming a layered structure, the layered structure comprising a resist layer disposed on the surface of the substrate, the resist layer comprising the resin, the base quencher, and the compound;

optionally baking the resist layer;

exposing the resist layer pattern-wise to radiation, thereby forming an exposed resist layer comprising exposed regions of the resist layer and non-exposed regions of the resist layer, the exposed regions of resist layer comprising an acid formed by exposing the compound to the radiation;

heating the exposed resist layer, thereby forming a heated exposed resist layer comprising heated exposed regions and heated non-exposed regions; and selectively removing the heated exposed regions or the heated non-exposed regions, thereby forming a patterned resist layer disposed on the surface of the substrate.

21. The method of claim 20, comprising transferring the patterned resist layer to the substrate.

22. The method of claim 20, comprising heating the patterned resist layer at a temperature effective in forming an acid by a thermal reaction of the compound, thereby forming a patterned resist layer that is soluble in the given alkaline developer.

23. The method of claim 20, wherein the heated exposed regions are selectively removed using an given alkaline developer, and the patterned resist layer comprises the heated non-exposed regions.

24. The method of claim 20, wherein the heated non-exposed regions are selectively removed using an organic developer, and the patterned resist layer comprises the heated exposed regions.

* * * * *